(12) United States Patent
Taniguchi et al.

(10) Patent No.: US 7,476,237 B2
(45) Date of Patent: Jan. 13, 2009

(54) SURGICAL INSTRUMENT

(75) Inventors: Kazunori Taniguchi, Hachioji (JP); Toru Nagase, Tachikawa (JP)

(73) Assignee: Olympus Corporation, Tokyo (JP)

( * ) Notice: Subject to any disclaimer, the term of this patent is extended or adjusted under 35 U.S.C. 154(b) by 1053 days.

(21) Appl. No.: 10/784,634

(22) Filed: Feb. 23, 2004

(65) Prior Publication Data
US 2004/0193212 A1    Sep. 30, 2004

(30) Foreign Application Priority Data
Feb. 27, 2003  (JP)  ............... 2003-051849
Feb. 27, 2003  (JP)  ............... 2003-051850
Feb. 27, 2003  (JP)  ............... 2003-051851

(51) Int. Cl.
*A61B 17/28* (2006.01)
*A61B 17/14* (2006.01)

(52) U.S. Cl. ................... 606/205; 606/207

(58) Field of Classification Search ........... 606/205, 606/206, 207
See application file for complete search history.

(56) References Cited

U.S. PATENT DOCUMENTS 1,359,391 A * 11/1920  Landymore et al. ............ 213/3

| | | |
|---|---|---|
| 5,275,608 A | 1/1994 | Forman et al. |
| 5,330,502 A | 7/1994 | Hassler et al. |
| 5,383,888 A | 1/1995 | Zvenyatsky et al. |
| 5,549,637 A | 8/1996 | Crainich |
| 6,936,061 B2 * | 8/2005 | Sasaki ................... 606/205 |

* cited by examiner

*Primary Examiner*—Vy Q. Bui
(74) *Attorney, Agent, or Firm*—Scully, Scott, Murphy & Presser, P.C.

(57) ABSTRACT

A surgical instrument includes a tubular member, a partition member for partitioning the inside of the tubular member, first and second shafts movable in forward and backward directions, an end effector, a base member connected to the second shaft, a supporting pin for supporting the base member to mount the end effector on the tubular member, a first connection member being movable in both forward and backward directions in the base member to open and close jaws connected to the end effector, a second connection member being movable through a joint formed by the supporting pin, a first operation control portion for manipulating the end effector via the first shaft, and a second operation control portion for moving the second shaft in both forward and backward directions to control the angle of the joint.

9 Claims, 31 Drawing Sheets

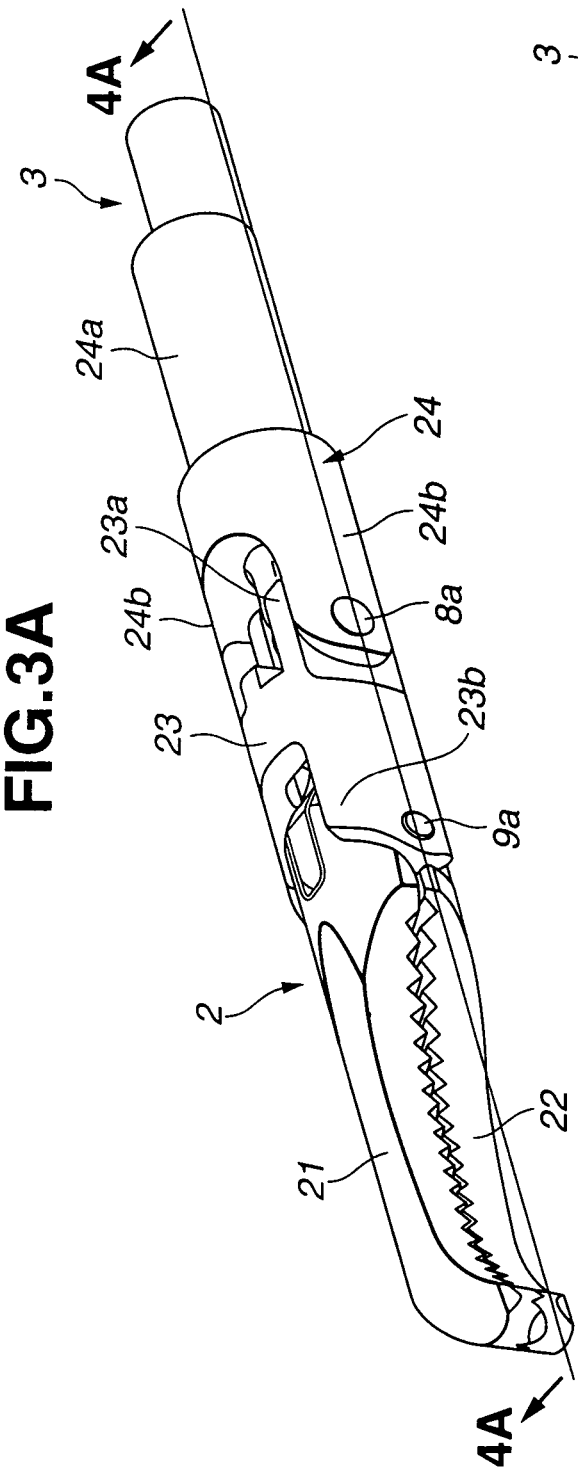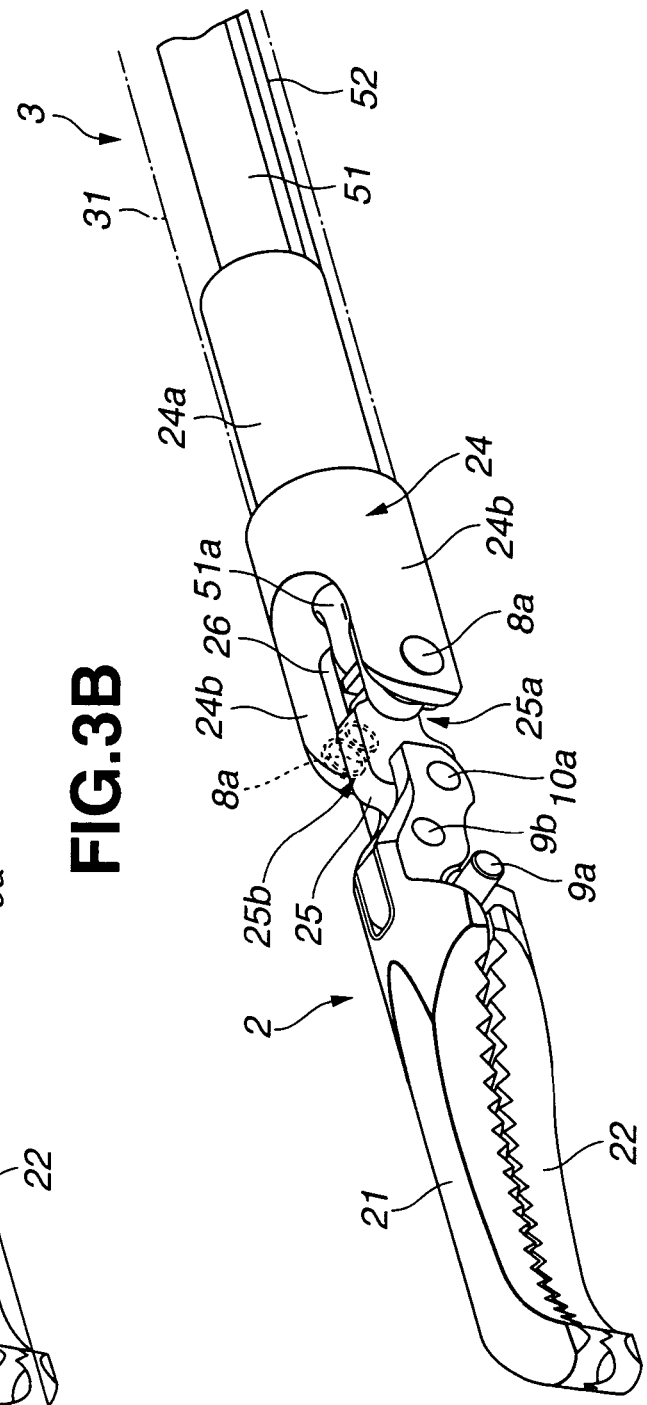

SURGICAL INSTRUMENT

This application claims benefit of Japanese Application No. 2003-051849 filed on Feb. 27, 2003, No. 2003-051850 filed on February 27, and No. 2003-051851 filed on Feb. 27, 2003, the contents of which are incorporated by this reference.

BACKGROUND OF THE INVENTION

1. Field of the Invention

The present invention relates to a surgical instrument for use in a surgical operation in which an end effector disposed on a distal end of the surgical instrument is operated by a human operator by manipulating a handle disposed on a proximal end of an insertion portion of the surgical instrument. More particularly, the present invention relates to a surgical instrument for use in endoscopic surgery.

2. Description of the Related Art

Conventionally, an endoscope is widely used to perform various surgical treatments on a body tissue while observing an image of the body tissue via the endoscope having an elongated insertion portion inserted in a body cavity. In recent years, endoscopes have been used to perform surgical treatments or procedures without having to perform a laparotomy and thus without imposing significant invasion against patients. In such endoscopic surgery, an endoscope for observation is introduced into a body cavity via a trocar, and a surgical instrument is introduced to a portion of interest in the body cavity via the trocar. While observing the surgical instrument and the portion of interest via the endoscope, a surgical treatment or procedure is performed.

Surgical instruments used in endoscopic surgery or the like are formed in an elongated shape, and an end effector disposed on an end of an insertion portion is manipulated by handling an operation control portion disposed on the opposite end.

A surgical instrument capable of rotating its end effector disposed on an end of an insertion portion is disclosed, for example, in U.S. Pat. Nos. 5,275,608, 5,330,502, 5,383,888, or 5,549,637.

More specifically, in a surgical instrument disclosed in U.S. Pat. No. 5,275,608, an end effector disposed on a distal end can be opened and closed by opening and closing a pair of handles disposed on a proximal end of the surgical instrument, and the end effector can be pivoted, that is, the orientation of the end effector can be changed, by rotating the pair of handles.

In a surgical instrument disclosed in U.S. Pat. No. 5,330,502, a treatment tool disposed on its distal end part can be opened and closed, and the distal end part can be pivoted in a direction away from the main axis of the treatment tool. In this surgical instrument, to realize the above capabilities, a rotation knob for rotating the distal end about the main axis is disposed at a location in front part of an operation handle, and a pivot control knob for pivoting the distal end part of the surgical instrument is disposed next to the rotation knob.

In a surgical instrument disclosed in U.S. Pat. No. 5,383,888, an end effector can be opened and closed by opening and closing a pair of handles disposed on the proximal end of the surgical instrument. Furthermore, in this surgical instrument, the end effector can be pivoted by operating a pivot control portion disposed on the proximal end.

In a surgical instrument disclosed in U.S. Pat. No. 5,549,637, a treatment tool attached to a distal end part of the surgical instrument can be operated. Furthermore, the distal end part can be pivoted in a direction away from the main axis of the treatment tool, and the treatment tool attached to the distal end part can be rotated about the axis independently. In this surgical instrument, the treatment tool is manipulated via a rigid base-side rod, a link substantially passing though a rotatable joint, and a head-side rod. Furthermore, in this surgical instrument, a rotation knob for rotating the main shaft is disposed in front part of the operation handle, at a distal-end side, to a manipulation handle, a pivot control knob is disposed next to the rotation control knob, and a rotation knob for independently rotating the treatment tool is disposed next to the pivot control knob.

SUMMARY OF THE INVENTION

The present invention provides a surgical instrument comprising a tubular member having a distal end and a proximal end, for forming a first axis, a partition member disposed in the tubular member in a direction along the axis of the tubular member, for partitioning the inside of the tubular member, a first shaft disposed in a first channel formed by the partition member such that the first shaft can move in both forward and backward directions, a second shaft disposed in a second channel formed by the partition member such that the second shaft can move in both forward and backward directions, an end effector including a pair of jaws, a base member connected to the second shaft, for supporting the end effector, a supporting pin for pivotably supporting the base member to mount the end effector on the distal end of the tubular member, a first connection member connected to the jaws, the first connection member being movable in both forward and backward directions in the base member to open and close the jaws, a second connection member for connecting the first connection member with the first shaft, the second connection member being movable through a joint formed by the supporting pin, a first operation control portion connected to the proximal end of the first shaft, for manipulating the end effector via the first shaft, and a second operation control portion connected with the proximal end of the second shaft, the second operation control portion being movable in both forward and backward directions to control the angle of the joint.

In this surgical instrument, if the first operation control portion is operated, the first shaft is moved forwardly or backwardly by an amount corresponding to an amount by which the first operation control portion is operated, and thus the end effector is manipulated in accordance with the operation performed on the first operation control portion. On the other hand, when the second operation control portion is operated, the second shaft is moved forwardly or backwardly by an amount corresponding to an amount by which the second operation control portion is operated, and the end effector base is pivoted by a corresponding amount. As a result, the end effector moves to a specified position.

The above and other objects, features and advantages of the invention will become more clearly understood from the following description referring to the accompanying drawings.

BRIEF DESCRIPTION OF THE DRAWINGS

FIG. 3A is a perspective view of an end effector;

FIG. 3B is a perspective view showing the end effector in a state in which an end effector base is removed;

DETAILED DESCRIPTION OF THE PREFERRED EMBODIMENTS

The present invention is described in further detail below with reference to specific embodiments in conjunction with the drawings.

Referring to FIGS. 1 to 20, a first embodiment of the present invention is described below. FIGS. 1 to 10 show the structure of a surgical instrument, and FIGS. 11 to 20 show the operation of the surgical instrument.

Figure 1:
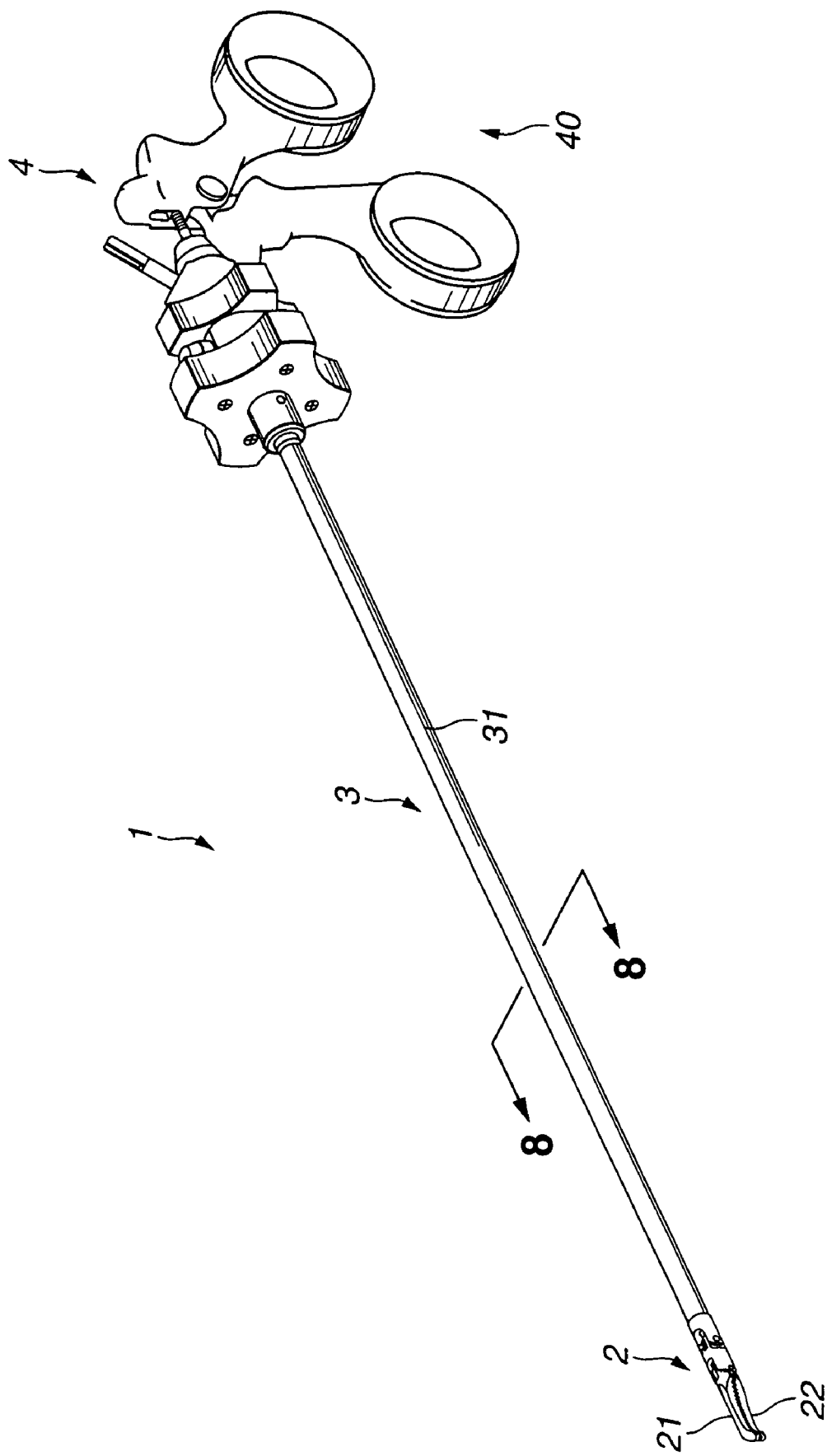
FIG. 1 is a perspective view of a surgical instrument.

As shown in FIG. 1, the surgical instrument 1 according to the present embodiment is constituted mainly of an end effector 2, an insertion portion 3, and a grasp control portion 4.

For example, the end effector 2 is a dissecting forceps including a pair of first and second jaws 21 and 22 that are formed of a rigid material such that they can be opened and closed. The insertion portion 3 includes an insertion tube 31 formed in the shape of an elongated tube serving as an outer sheath. The grasp control portion 4 includes a first operation control portion serving as an end effector manipulation portion 40.

Figure 2:
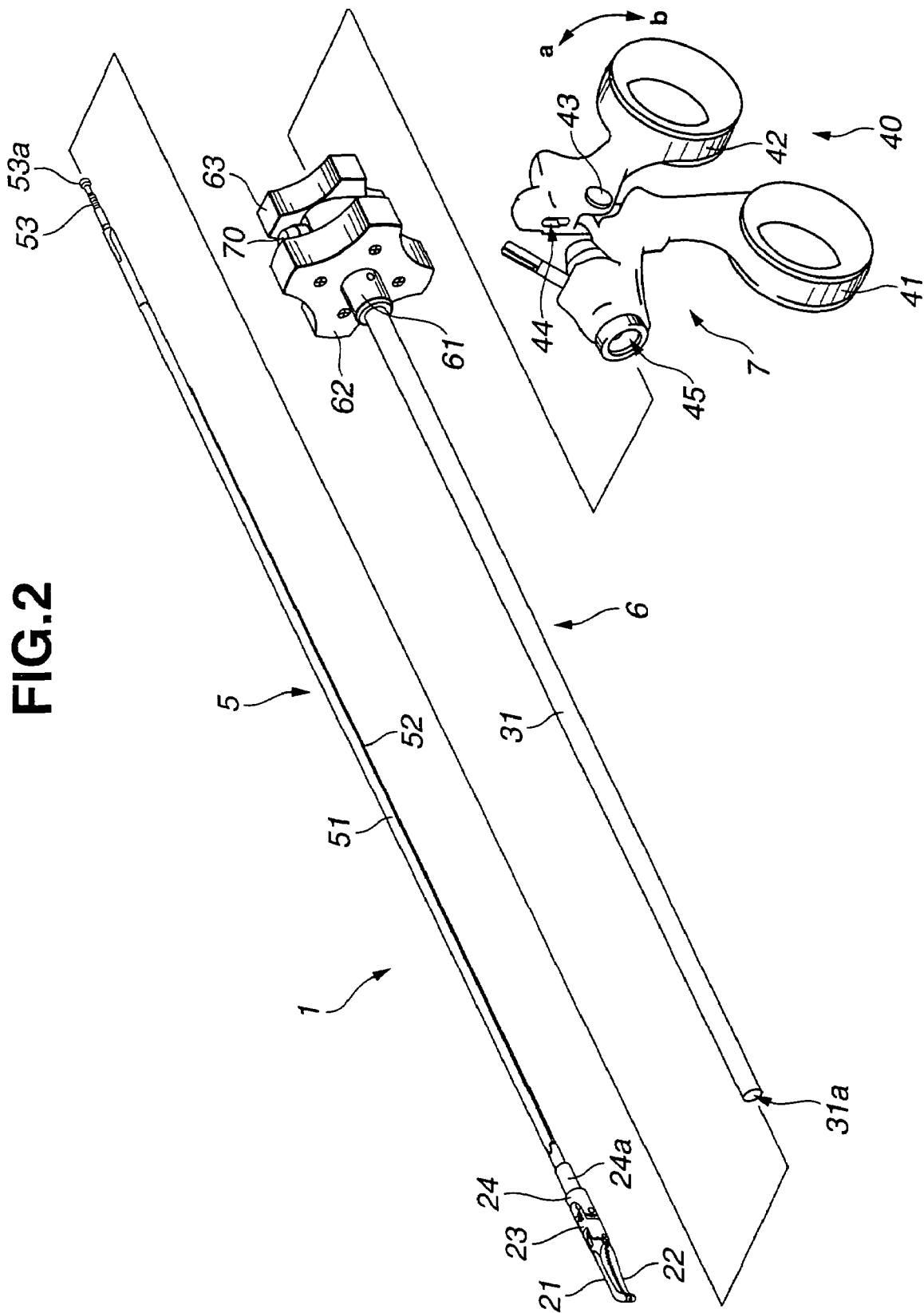
FIG. 2 is a perspective view showing the structure of the surgical instrument.

As shown in FIG. 2, the surgical instrument 1 can be separated into an end effector assembly 5, an insertion portion assembly 6, and a manipulation portion assembly 7.

The end effector assembly 5 is constituted mainly of the jaws 21 and 22, an end effector base 23 serving as a base member, a distal end cover 24, an end effector manipulation rod 51, and an end effector base manipulation rod 52.

The proximal end of each of the jaws 21 and 22 is connected to the end effector base 23. The distal end cover 24 is disposed on a distal end of the insertion tube 31. The end effector manipulation rod 51 is a first shaft formed of a rigid material so as to have a particular length. The end effector base manipulation rod 52 is a second shaft formed of a rigid material so as to have a particular length.

The end effector manipulation rod 51 and the end effector base manipulation rod 52 are inserted in parallel through the insertion tube 31. A connecting rod 53 having a ball 53a is integrally connected with the proximal end of the end effector manipulation rod 51.

The insertion portion assembly 6 is constituted mainly of the insertion tube 31, a pivot base 61, a pivot control knob 62, and a rotation knob 63. The pivot base 61 is disposed on a proximal end of the insertion tube 31. The pivot control knob 62 serves as a second operation control portion. The rotation knob 63 serves as a third operation control portion. A release button 70 is disposed between the pivot control knob 62 and the rotation knob 63. The release button 70 is used when the insertion portion assembly 6 is removed from the manipulation portion assembly 7.

When the end effector assembly 5 is assembled with the insertion portion assembly 6, a small-diameter portion 24a of the distal end cover 24 is fit into an opening 31a at the distal end of the insertion tube 31, and the end effector assembly 5 is inserted into the insertion portion assembly 6 such that the end effector manipulation rod 51 and the connecting rod 53 partially protrude from a proximal end of the insertion tube 31. The proximal end of the end effector base manipulation rod 52 is connected with the pivot base 61 using a connection screw denoted by reference numeral 67 in FIG. 10.

The manipulation portion assembly 7 is constituted mainly of a fixed handle 41 and a movable handle 42. The fixed handle 41 and the movable handle 42 form the end effector manipulation portion 40. The fixed handle 41 and the movable handle 42 are pivotably connected via a handle pin 43.

The movable handle 42 can pivot in either direction denoted by an arrow a in FIG. 2 or denoted by arrow b. A connecting rod receiving hole 44 is formed on a distal end of the movable handle 42. The ball 53a of the connecting rod 53 is removably fit in the connecting rod receiving hole 44. An attaching portion 45 is formed on a distal end of the fixed handle 41 such that the insertion portion assembly 6 can be removably attached to the attaching portion 45.

To assemble the end effector assembly 5, the insertion portion assembly 6, and the manipulation portion assembly 7 into the surgical instrument 1 shown in FIG. 1, the end effector assembly 5 and the insertion portion assembly 6 are first combined together. Thereafter, the end effector assembly 5 and the insertion portion assembly 6 in the combined form are connected with the manipulation portion assembly 7. More specifically, the proximal end part of the insertion portion assembly 6 is fit into the attaching portion 45 of the manipulation portion assembly 7, and the ball 53a of the connecting rod 53 of the end effector assembly 5 is fit into the connecting rod receiving hole 44.

Referring to FIGS. 3A to 10, the structure of the surgical instrument 1 is described in further detail below.

First, the end effector assembly 5 is described referring to FIGS. 3A to 4B.

The end effector assembly 5 has an opening/closing link mechanism and a pivot link mechanism. The opening/closing link mechanism is a mechanism for opening and closing the first jaw 21 and the second jaw 22 of the end effector 2. The pivot link mechanism is a mechanism for changing the position of the end effector 2 with respect to the axial direction of the insertion portion 3.

The pivot link mechanism includes a pair of first pivot pins 8a for connecting a cover projection part 24b of the distal end cover 24 with a proximal-end projection 23a of the end effector base 23 and also includes a second pivot pin 8b for connecting the proximal end of the end effector base 23 with a distal end unit 52a of the end effector base manipulation rod 52.

The opening/closing link mechanism includes a first opening/closing pin 9a for connecting distal-end projections 23b of the end effector base 23 with the second jaw 22, a second opening/closing pin 9b for connecting the second jaw 22 and the first jaw 21, a first connection pin 10a for connecting a proximal end part of the first jaw 21 with a proximal end part of a first connection member 25, a second connection pin 10b for connecting the first connection member 25 with a second connection member 26, and a third connection pin 10c for connecting the end effector manipulation rod 51 with the second connection member 26.

The end effector base 23 and the distal end cover 24 are formed in substantially tubular shape using a material having proper rigidity and flexibility. A small-diameter portion 24a is formed on a proximal end of the distal end cover 24. The small-diameter portion 24a is inserted through the distal end opening 31a into the insertion tube 31 of the insertion portion 3. On the other hand, a pair of projections 23a and a pair of projections 23b are formed on the distal end and the proximal end, respectively, of the end effector base 23.

Figure 4A:
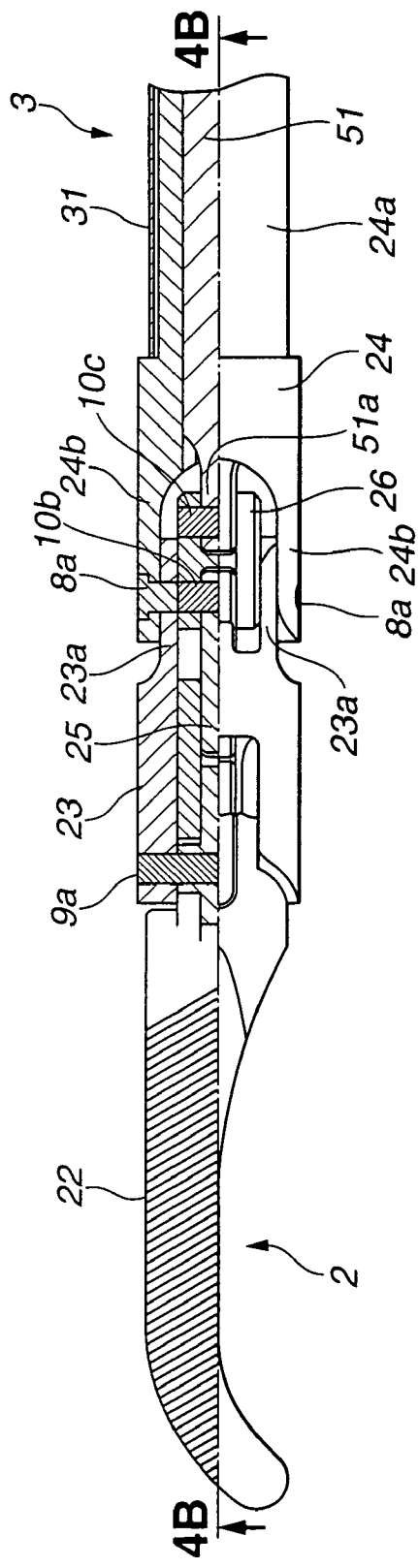
FIG. 4A is a cross-sectional view taken along line 4A-4A of FIG. 3A.

The first connection member 25 is formed of a plate-shaped rigid material. The second connection member 26 is also formed of a rigid material. As shown in FIG. 4A, the second connection member 26 has an H-like shape in cross section, and recessed parts are formed on both end portions thereof. A flat plate-shaped distal end part 51a formed on the distal end of the end effector manipulation rod 51 is connected with the recessed part on the proximal end of the second connection member 26 by the third connection pin 10c. On the other hand, the proximal end of the first connection member 25 is connected with the recessed part on the head of the second connection member 26 by the second connection pin 10b.

The distal end cover 24 has a pair of cover projection parts 24b. The pair of proximal-end projections 23a and the second connection member 26 are disposed between the cover projection parts 24b. Note that the proximal-end projections 23a are formed on the proximal end of the end effector base 23.

The structure of the pivot link mechanism is described below.

The proximal-end projections 23a of the end effector base 23 are connected with the cover projection parts 24b of the distal end cover 24 by the pair of first pivot pins 8a so as to form a pivotable joint. Note that the first pivot pins 8a are disposed in a direction perpendicular to the axis of the insertion portion 3.

The distal end unit 52a of the end effector base manipulation rod 52 is connected with the proximal end of the end effector base 23 by the second pivot pin 8b. The second pivot pin 8b is disposed parallel to the first pivot pins 8a.

Figure 4B:
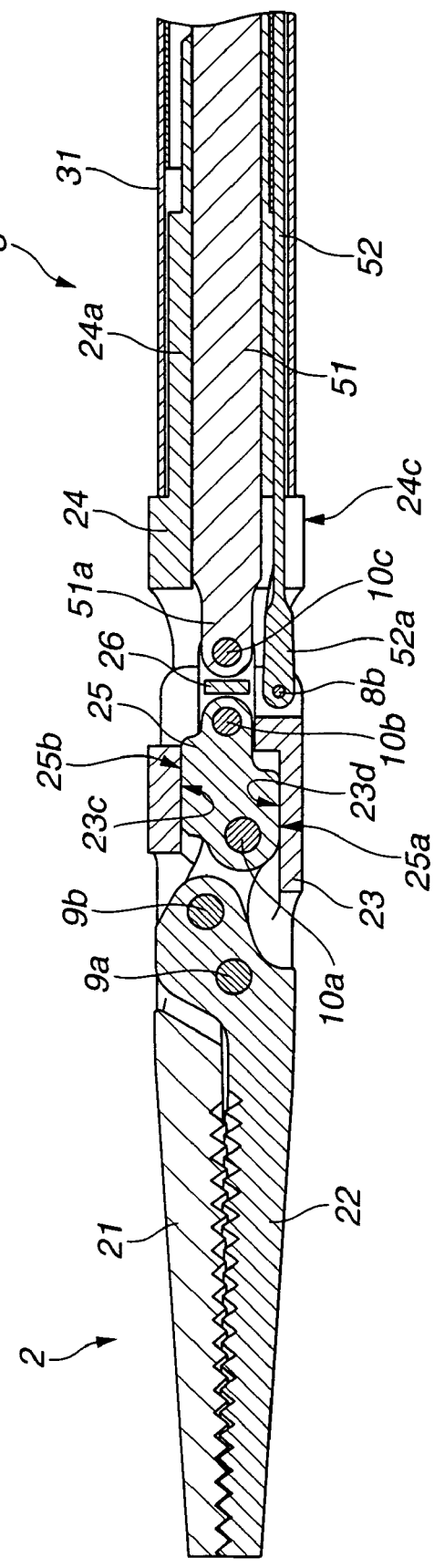
FIG. 4B is a cross-sectional view taken along line 4B-4B of FIG. 4A.

The end effector base manipulation rod 52 is disposed in a cutout channel 24c formed at a particular location in the distal end cover 24. The location of the second pivot pin 8b in the state shown in FIG. 4B is referred to as a zero pivot end, while the location of the second pivot pin 8b represented by a solid line in FIG. 5 is referred to as a maximum pivot end.

Figure 5:
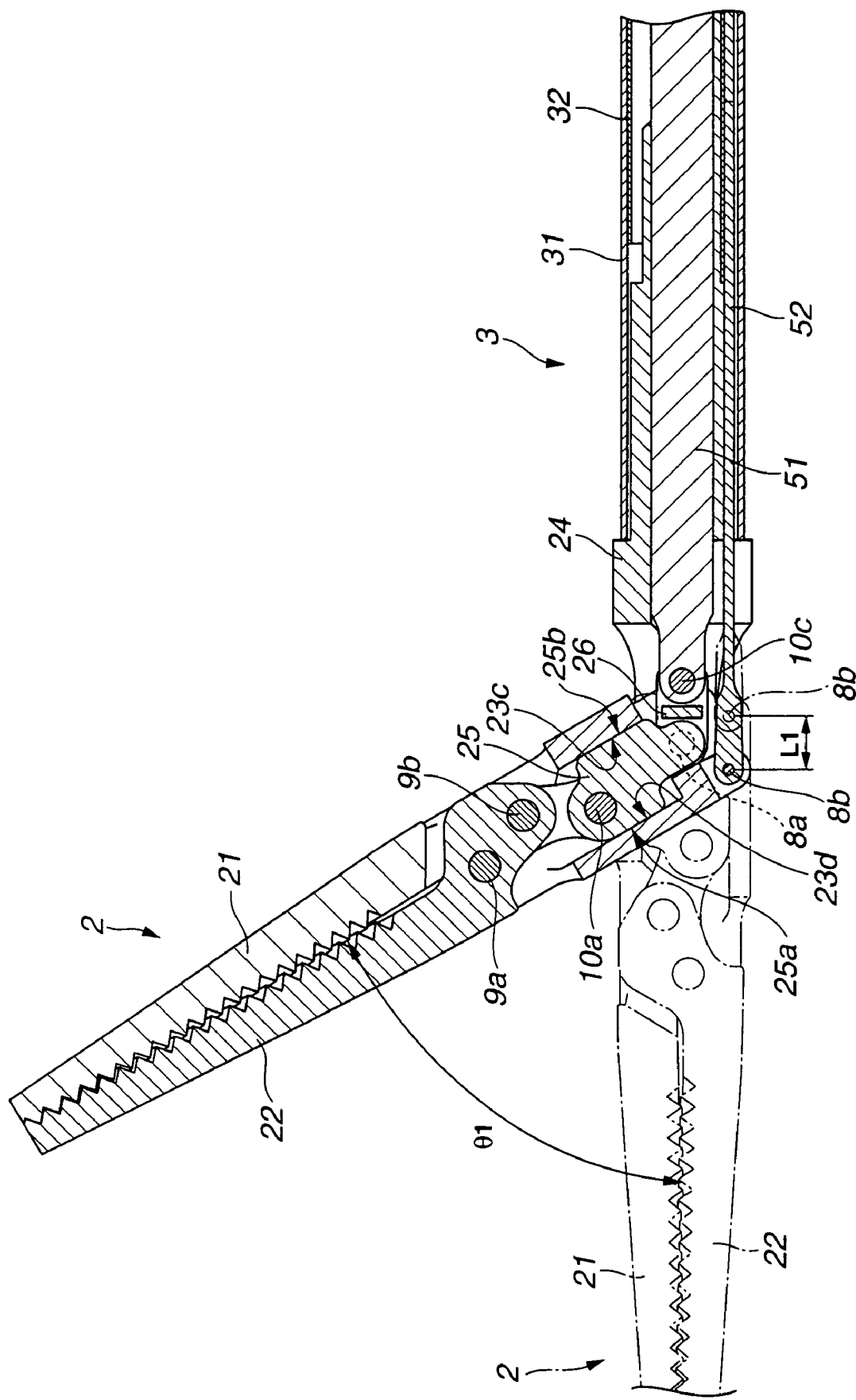
FIG. 5 is a diagram showing a manner in which an end effector pivots.

As shown in FIG. 5, if the second pivot pin 8b pivotably supporting the end effector base manipulation rod 52 is moved a linear distance $L_1$ from the zero pivot end represented by a dashed line to the maximum pivot end represented by the solid line, the end effector base 23 pivots on the first pivot pins 8a represented by a broken line until it comes into a position represented by solid lines.

As a result, the end effector 2 formed of the first jaw 21 and the second jaw 22 comes into a pivoted position represented by dashed lines at an angle $\theta_1$ with respect to the horizontal direction. That is, by moving the location of the distal end of the end effector base manipulation rod 52 by a proper distance within the range from the zero pivot end to the maximum pivot end, the end effector 2 can be moved into a desired position within the range of angle $\theta_1$.

Now, the opening/closing link mechanism is described below.

The first opening/closing pin 9a is fixed to the distal-end projections 23b of the end effector base 23. Note that the first opening/closing pin 9a is disposed parallel to the first pivot pins 8a. The first opening/closing pin 9a is connected to a middle part of the second jaw 22 such that the second jaw 22 can pivot on the first opening/closing pin 9a. Thus, the second jaw 22 can pivot on the first opening/closing pin 9a with respect to the end effector base 23.

The second opening/closing pin 9b is disposed in the proximal end part of the second jaw 22. The second opening/closing pin 9b is connected with a middle part of the first jaw 21 such that the first jaw 21 can pivot on the second opening/closing pin 9b. Thus, the first jaw 21 and the second jaw 22 can pivot with respect to each other on the second opening/closing pin 9b. By pivoting the first jaw 21 and the second jaw 22 with respect to each other, the end effector 2 can be opened or closed.

The proximal end of the first jaw 21 is pivotably connected to the distal end of the first connection member 25 by the first connection pin 10a. Side faces 25a and 25b of the first connection member 25 are in contact with contact faces 23c and 23d of the end effector base 23. Thus, the first connection member 25 moves longitudinally in the end effector base 23 in a direction parallel to the contact faces 23c and 23d.

The other end of the first connection member 25 is located in the recess of the distal end of the second connection member 26. The first connection member 25 and the second connection member 26 are connected with each other via the second connection pin 10b.

On the other hand, the flat plate-shaped distal end part 51a of the end effector manipulation rod 51 is located in the recess of the distal end part of the second connection member 26. The end effector manipulation rod 51 and the second connection member 26 are connected with each other via the third connection pin 10c.

Thus, the end effector manipulation rod 51 and the end effector 2 are connected with each other via the second connection member 26 and the first connection member 25.

Figure 6:
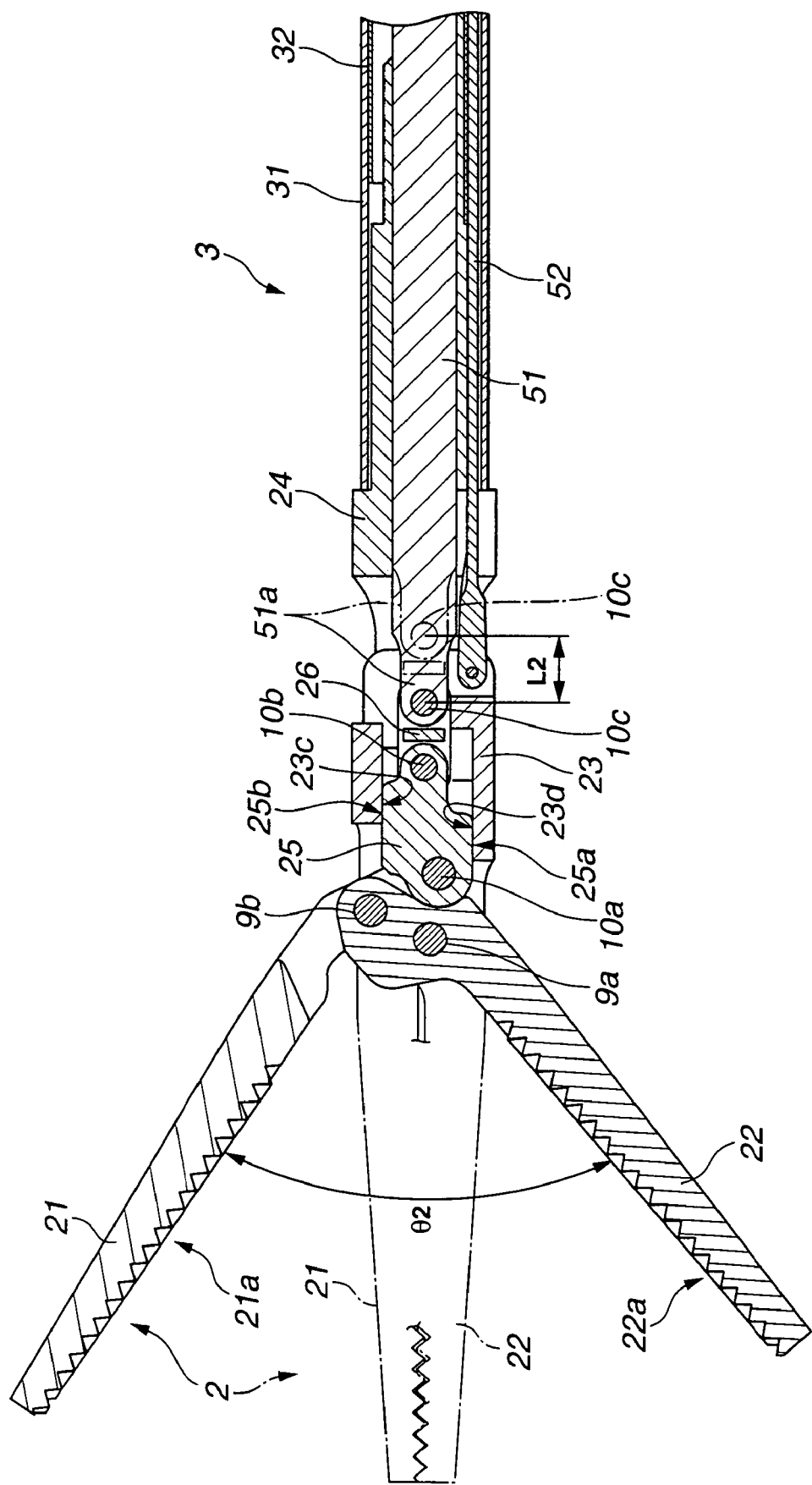
FIG. 6 is a diagram showing a manner in which jaws are opened and closed when the end effector is in a non-pivoted state.
Figure 7:
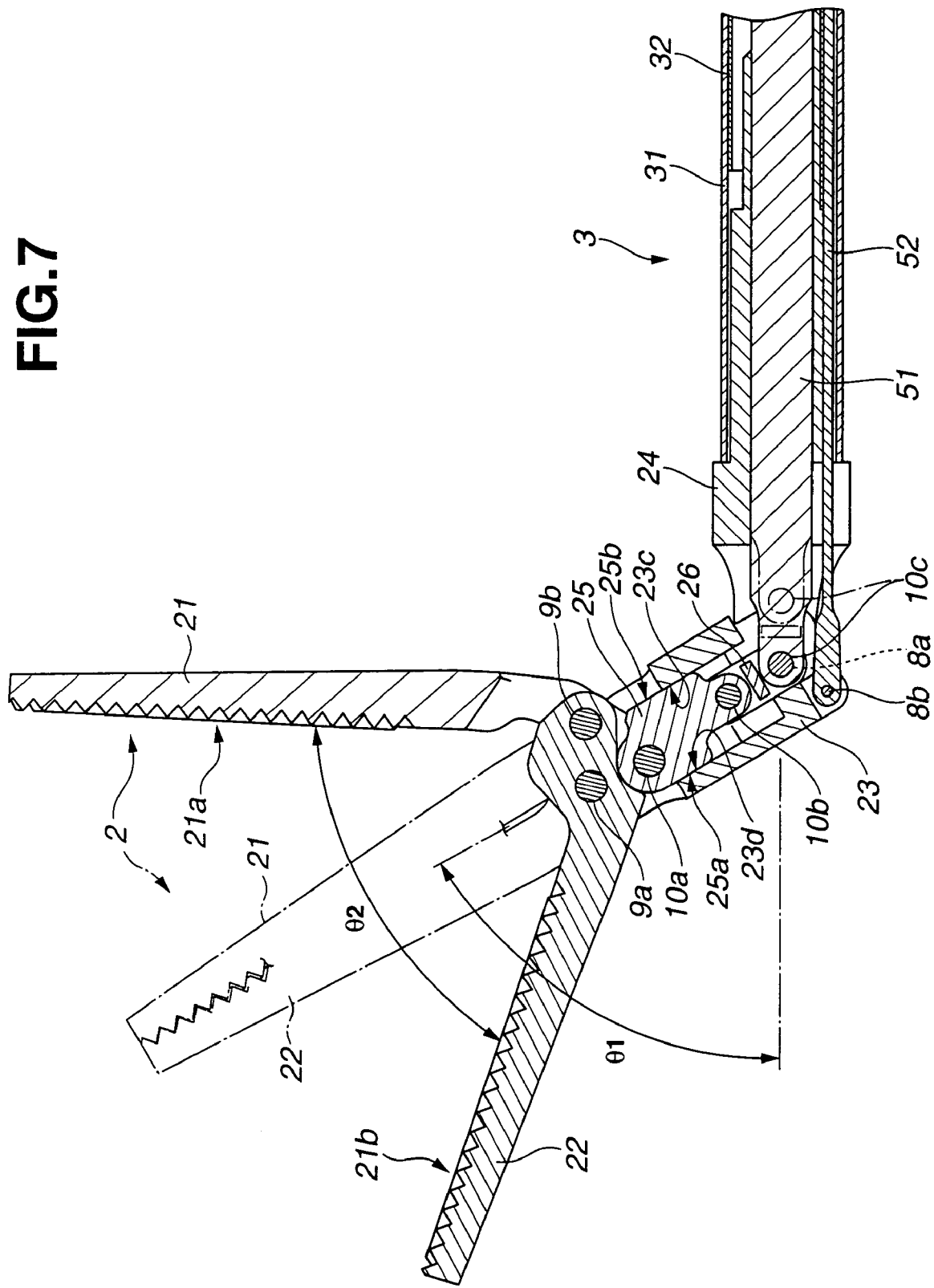
FIG. 7 is a diagram showing a manner in which jaws are opened and closed when the end effector is in a fully-pivoted position.

The location of the third connection pin 10c in the state shown in FIG. 4B is referred to as a first end position where the first jaw 21 and the second jaw 22 of the end effector 2 are in the closed state. On the other hand, the location of the third connection pin 10c in the state shown in FIG. 6 or 7 is referred to as a second end position where the first jaw 21 and the second jaw 22 of the end effector 2 are in the fully opened state.

The distance between through-holes of the second connection member 26 in which the second connection pin 10b and the third connection pin 10c are respectively disposed is referred to as a pin-to-pin distance. The pin-to-pin distance is set to a particular value such that conditions described below are satisfied.

When the end effector 2 is in a closed state as shown in FIG. 4A or 4B, the central axis of the second connection pin 10b and the central axis of the first pivot pin 8a lie in the same line. On the other hand, when the end effector 2 is in a fully opened state as shown in FIG. 6 or 7, which will be referred to again later, the central axis of the third connection pin 10c and the central axis of the first pivot pin 8a lie in the same line.

Thus, when the first jaw 21 and the second jaw 22 forming the end effector 2 are in the closed state, if the end effector 2 is pivoted, the first connection member 25 pivots on the second connection pin 10b. As a result, as shown in FIG. 5, the first jaw 21 and the second jaw 22 are maintained in the closed state.

On the other hand, when the first jaw 21 and the second jaw 22 of the end effector 2 are in the opened state, if the end effector 2 is pivoted, the first connection member 25 and the second connection member 26 pivot on the third connection pin 10c. As a result, as shown in FIG. 7, the first jaw 21 and the second jaw 22 are maintained in the opened state.

Therefore, if the distal end of the end effector manipulation rod 51 is moved a linear distance L2 from the first end position represented by dashed lines to the second end position represented by solid lines as shown in FIG. 6 or 7, the first connection member 25 moves in the end effector base 23 in a direction parallel to the end effector base 23, and the first jaw 21 and the second jaw 22 pivot on the second opening/closing pin 9b and the first opening/closing pin 9a, respectively. As a result, the end effector 2 changes from the closed state represented by dashed lines to a fully opened state with an angle of $\theta_2$.

That is, by moving the location of the distal end of the end effector manipulation rod 51 by a proper distance within the range from the first end position to the second end position, the first jaw 21 and the second jaw 22 of the end effector 2 can be opened to a desired angle within $\theta_2$.

The first jaw 21 has a grasping surface 21a, and the second jaw 22 has a grasping surface 22a, wherein the grasping surfaces 21a and 22a face each other. In the present embodiment, protrusions and depressions are formed on the grasping surfaces 21a and 22a. Note that the shapes of the jaws 21 and 22 are not limited to those shown in FIG. 6 or 7, and the manner of forming protrusion and depressions is not limited to that shown in FIG. 6 or 7. Furthermore, the end effector 2 is not limited to that having jaws shown in FIG. 6 or 7, but any other end effector such as a scissors forceps, a grasping forceps, or a stapler may also be employed. In the embodiment described above, the side faces of the first connection member 25 are in contact with the contact surfaces 23c and 23d of the end effector base 23. Alternatively, a guide groove may be formed on the end effector base 23, and a guide pin engaged in the guide groove may be formed on the first connection member 25.

Figure 8:
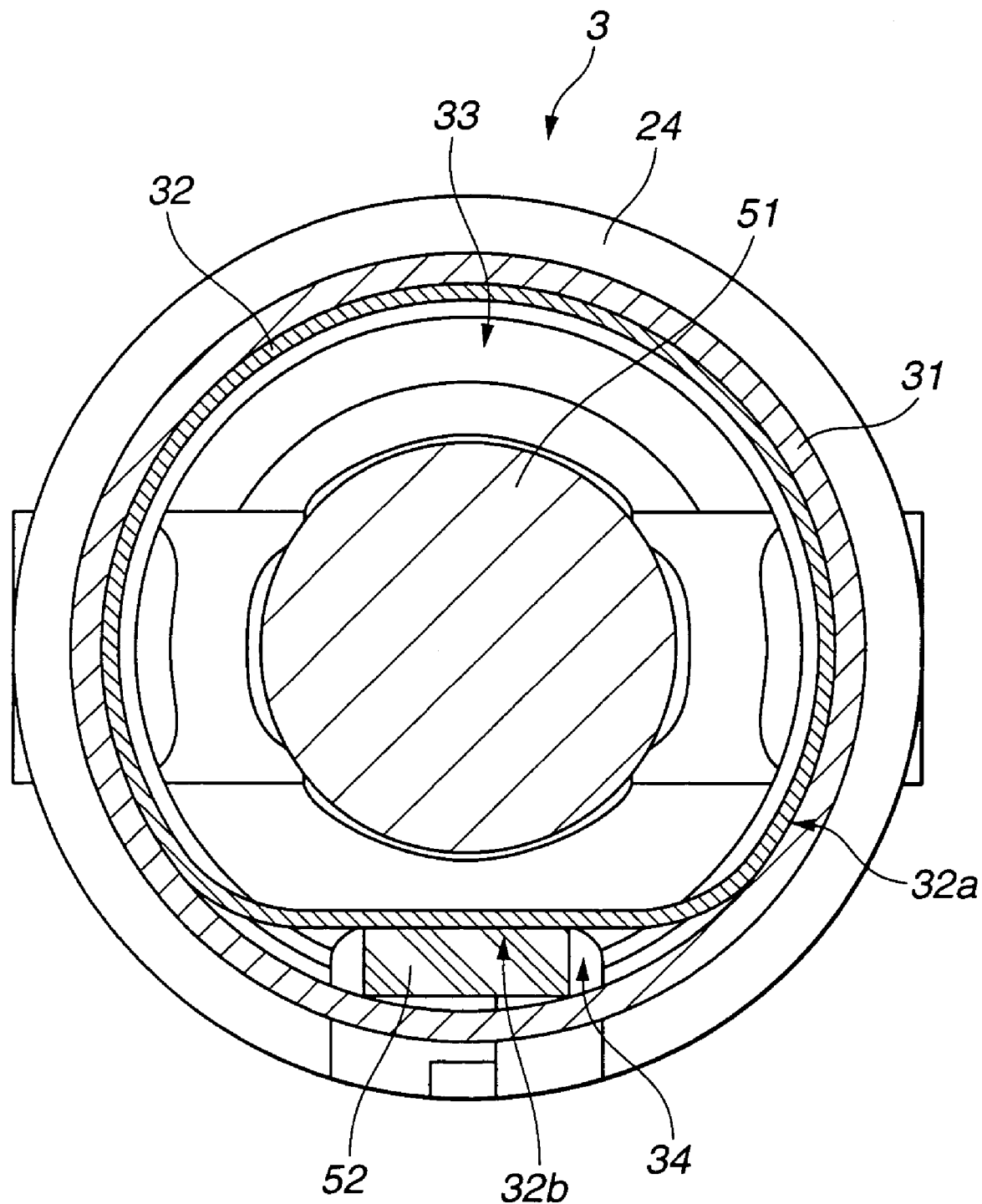
FIG. 8 is a cross-sectional view taken along line 8-8 of FIG. 1.

As shown in FIG. 8, the end effector manipulation rod 51 of the opening/closing link mechanism and the end effector base manipulation rod 52 of the pivot link mechanism are inserted in parallel through the insertion portion 3 of the insertion portion assembly 6 such that they independently move in both forward and backward directions. The insertion portion 3 includes an insertion tube 31 serving as an outer sheath and an inner tube 32 serving as a partition that partitions the inside of the insertion tube 31 into a plural parts. The inner tube 32 has a particular cross-sectional shape. The insertion tube 31 and the inner tube 32 are formed of a rigid material such as stainless steel.

In the present embodiment, the inner tube 32 includes a round-shaped circumferential portion 32a and a flat part 32b. The round-shaped circumferential portion 32a is in intimate contact with the inner surface of the insertion tube 31, while the flat part 32b forms, in conjunction with the inner surface of the insertion tube 31, a through-hole that is rectangular in cross section. The end effector base manipulation rod 52 is inserted through this through-hole, and the end effector manipulation rod 51 is inserted through the inner hole of the tube 32.

That is, by disposing the inner tube 32 in the insertion tube 31 such that the round-shaped circumferential portion 32a is in contact with the inner surface of the insertion tube 31, a first channel 33 and a second channel 34 are formed in the inside of the insertion portion 3. More specifically, the first channel 33 is formed by the inner hole of the inner tube 32 and the end effector manipulation rod 51 is inserted through the first channel 33, and the second channel 34 is used as a through-hole through which the end effector base manipulation rod 52 is inserted.

In the second channel 34 according to the present embodiment, the size of the opening in a direction corresponding to the thickness of the end effector base manipulation rod 52 is set to be substantially equal to the thickness of the end effector base manipulation rod 52 to prevent the end effector base manipulation rod 52 from bending. This makes it possible to transmit a force in an axial direction by moving the end effector base manipulation rod 52 having an elongated shape and having a small thickness along the axial direction without causing the end effector base manipulation rod 52 to bend. That is, it is ensured that a force is transmitted in the axial direction via the end effector base manipulation rod 52 in a highly reliable fashion.

Note that the partition member is not limited to the inner tube 32 described above, but a plate or the like may be disposed in the insertion tube 31 to form the first channel 33 and the second channel 34.

Figure 9:
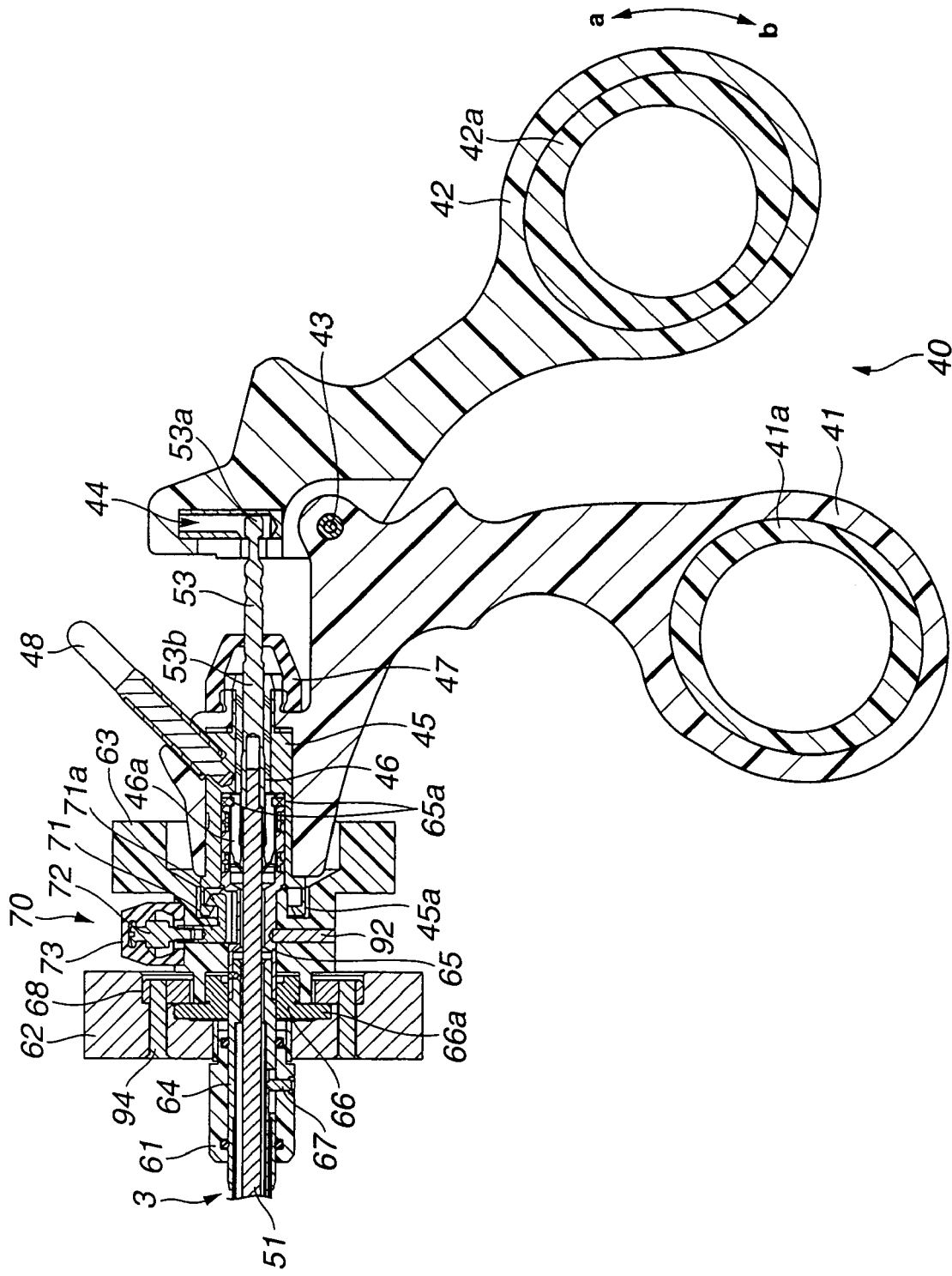
FIG. 9 is a cross-sectional view showing the structure of an insertion portion assembly and that of a manipulation portion assembly.
Figure 10:
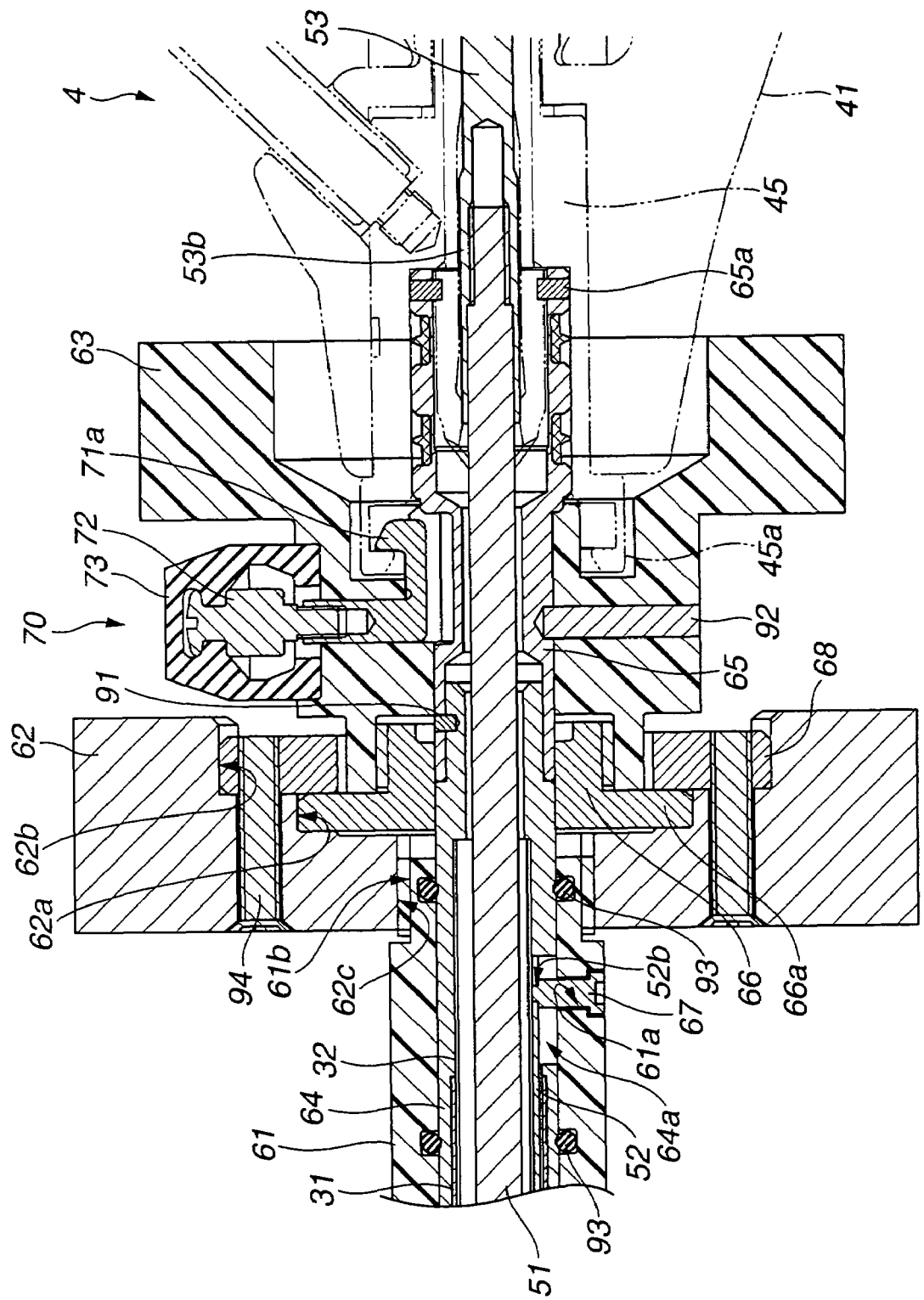
FIG. 10 is an enlarged view of a proximal end part of the insertion portion assembly shown in FIG. 9.

As shown in FIGS. 9 and 10, the pivot control knob 62 and the rotation knob 63 are disposed on the proximal end of the insertion portion 3, at closely spaced locations close to the end effector manipulation portion 40. The pivot control knob 62 and the rotation knob 63 are operated with a finger of one hand by which the end effector manipulation portion 40 is held. To this end, the external diameter of the pivot control knob 62 is set to be greater than the external diameter of the rotation knob 63. More specifically, in the present embodiment, the external diameter of the pivot control knob 62 is set to be 1.2 times greater than the external diameter of the rotation knob 63.

The insertion tube 31 and the inner tube 32 forming the insertion portion 3 are set so as to have particular lengths and particular diameters. A first base tube 64 is fixed to the proximal end of the insertion tube 31 and the proximal end of the inner tube 32. A second base tube 65 is integrally connected with the first base tube 64 via a first fixing member 91.

The pivot base 61 is fit around the first base tube 64 such that the pivot base 61 can move in both directions along the axis. The pivot control knob 62 is fit around a tube formed by the first base tube 64 and the second base tube 65 such that the pivot control knob 62 can rotate around the tube. The pivot control knob 62 and the pivot base 61 are coupled with each other by means of screwing. On the other hand, the rotation knob 63 is integrally connected with the second base tube 65 via a second fixing part 92. The pivot control knob 62 is supported by a flange 66a formed on the rotation knob 63 such that the pivot control knob 62 is prevented from moving with respect to the tube thereby ensuring that the pivot control knob 62 can rotate at the same location. The pivot base 61 and the rotation knob 63 are made of a resin.

The structure is described in further detail below with reference to the drawings.

The end effector manipulation rod 51 is inserted through the first base tube 64. The proximal end parts of the insertion tube 31 and the inner tube 32 are disposed in a stepped hole formed in the inside of the first base tube 64. At a predetermined position in a side face of the first base tube 64, a long hole 64a is formed such that the long hole 64a communicates with the second channel 34 through which the end effector base manipulation rod 52 is inserted.

This makes it possible to get access to the proximal end part of the end effector base manipulation rod 52 inserted through the second channel 34 via the long hole 64a from the outside of the first base tube 64. A screw hole 61a communicating with the long hole 64a is formed at a predetermined position in a side face of the pivot base 61 that is fit around the first base tube 64 such that the pivot base 61 can move in both directions along the axis.

After the screw hole 61a is positioned with respect to the long hole 64a, the connection screw 67 is inserted into the screw hole 61a such that the connection screw 67 is screwed into an internal thread 52b formed in the proximal end part of the end effector base manipulation rod 52 thereby integrally connecting the end effector base manipulation rod 52 with the pivot base 61.

Thus, if the pivot base 61 is moved in a direction along the axis with respect to the first base tube 64, the connection screw 67 moves within the long hole 64a. In response, the motion of the connection screw 67 causes the end effector base manipulation rod 52 integrally connected with the pivot base 61 to move in a corresponding axial direction. As a result, the location of the distal end unit 52a changes within a range denoted by $L_1$ in FIG. 5.

For example, an O-ring 93 is disposed at a particular location along the inner circumference of the pivot base 61. The O-ring 93 prevents an abdominal cavity from communicating with the outside via the long hole 64a and the second channel 34.

On the other hand, a flange unit 66 having a flange 66a is disposed on the distal end of the rotation knob 63 integrally connected with the second base tube 65. The flange 66a of the flange unit 66 is disposed in a small-diameter stepped hole 62a with a particular depth and a particular diameter formed in the proximal end part, facing the rotation knob 63, of the pivot control knob 62.

A circular-shaped restriction ring 68 for supporting the flange 66a is disposed in a large-diameter hole 62b of the stepped hole. The restriction ring 68 is integrally fixed to the pivot control knob 62 by fixing screws 94. The restriction ring 68 restricts the motion of the pivot control knob 62 in a direction along the axis of the insertion portion 3 although the pivot control knob 62 is allowed to rotate with respect to the flange 66a.

An internal thread 62c is formed in the channel of the pivot control knob 62. An external thread 61b is formed on the proximal end part of the pivot base 61. The external thread 61b and the internal thread 62c are screwed together thereby connecting the pivot control knob 62 and the pivot base 61 with each other.

Thus, by rotating the pivot control knob 62 in a desired direction, the pivot base 61 can be moved with respect to the first base tube 64 in a forward or backward direction. As a result, the end effector base manipulation rod 52 integrally connected by the connection screw 67 with the pivot base 61 is moved in a forward or backward direction, and thus the location of the distal end unit 52a changes by a distance $L_1$ shown in FIG. 5.

When the pivot base 61 is at the location shown in FIG. 9, the distal end of the end effector base manipulation rod 52 is located at the zero pivot end shown in FIG. 4 or 6.

In order that the pivot control knob 62 can be easily rotated with a finger of one hand with which the surgical instrument 1 is held to move the pivot base 61 in a forward or backward direction, the pivot control knob 62 is formed so as to have a greater diameter than that of the rotation knob 63, a small-diameter hole 62a is formed such that its depth is greater by a particular amount than the thickness of the flange 66a, and a stepped portion is formed on the bottom of the small-diameter hole 62a of the pivot control knob 62 so as to minimize the contact area between the flange 66a and the bottom surface of the small-diameter hole 62a.

Furthermore, the end effector manipulation rod 51 and the rotation knob 63 are disposed such that they are substantially coaxial thereby allowing the insertion portion 3 to rotate about the central axis of the rotation knob.

The release button 70 is located between the pivot control knob 62 and the rotation knob 63. The release button 70 is a release mechanism formed of a first management member 71 having a locking hook 71a, a management pin 72, and a button 73 made of an elastic material. The first management member 71 is disposed on the rotation knob 63.

Thus, the grasp control portion 4 represented by a two-dash line in FIG. 10 can be attached and removed by operating the button 73 of the release button 70 thereby changing the location of the locking hook 71a.

Now, referring to FIG. 9, the manipulation portion assembly 7 is described below.

The fixed handle 41 and the movable handle 42 forming the end effector manipulation portion 40 are made of a resin. Rings 41a and 42a are attached to the fixed handle 41 and the movable handle 42, respectively, so that the rings 41a and 42a reduces burdens on fingers of an operator.

The connecting rod receiving hole 44 is formed in the head portion of the movable handle 42. On the other hand, the attaching portion 45 having a channel through which the end effector manipulation rod 51 integrally connected with the connecting rod 53 is inserted is formed in the head portion of the fixed handle 41. A management member 45a, with which the locking hook 71a is engaged, is formed on the distal end part of the attaching portion 45. The fixed handle 41 has a channel through which the connecting rod 53 is inserted.

An end effector manipulation rod receiving portion 46 is disposed in the channel of the attaching portion 45 such that the end effector manipulation rod receiving portion 46 can rotate about the axis. The end effector manipulation rod receiving portion 46 has a guide 46a formed on its distal-end side. The guide 46a receives a rotation guide pin 65a disposed on the distal end of the second base tube 65. Smooth side faces 53b of the connecting rod 53 are in contact with the end effector manipulation rod receiving portion 46.

Thus, when the rotation knob 63 is rotated, the end effector manipulation rod receiving portion 46 rotates together with the second base tube 65 of the insertion portion assembly 6, and the rotation of the end effector manipulation rod receiving portion 46 causes the end effector manipulation rod 51 to rotate. That is, by properly rotating the rotation knob 63, the location of the end effector 2 with respect to the end effector manipulation portion 40 can be changed.

The fixed handle 41 has a hermetic cap 47 that prevents the pressure in an abdominal cavity from decreasing due to leakage through the first channel 33. Furthermore, the fixed handle 41 has an RF power input pin 48. The inner tube 32 having the first channel 33 is formed so as to have an external diameter that allows the outer circumferential surface to be covered with an insulating tube (not shown in the figure). The insulating tube covering the inner tube 32 makes it possible to use RF power input via the RF power input pin 48 in a surgical treatment.

The operation of the surgical instrument 1 constructed in the above-described manner is described below.

First, the pivoting operation of the movable handle 42 is described.

Figure 11:
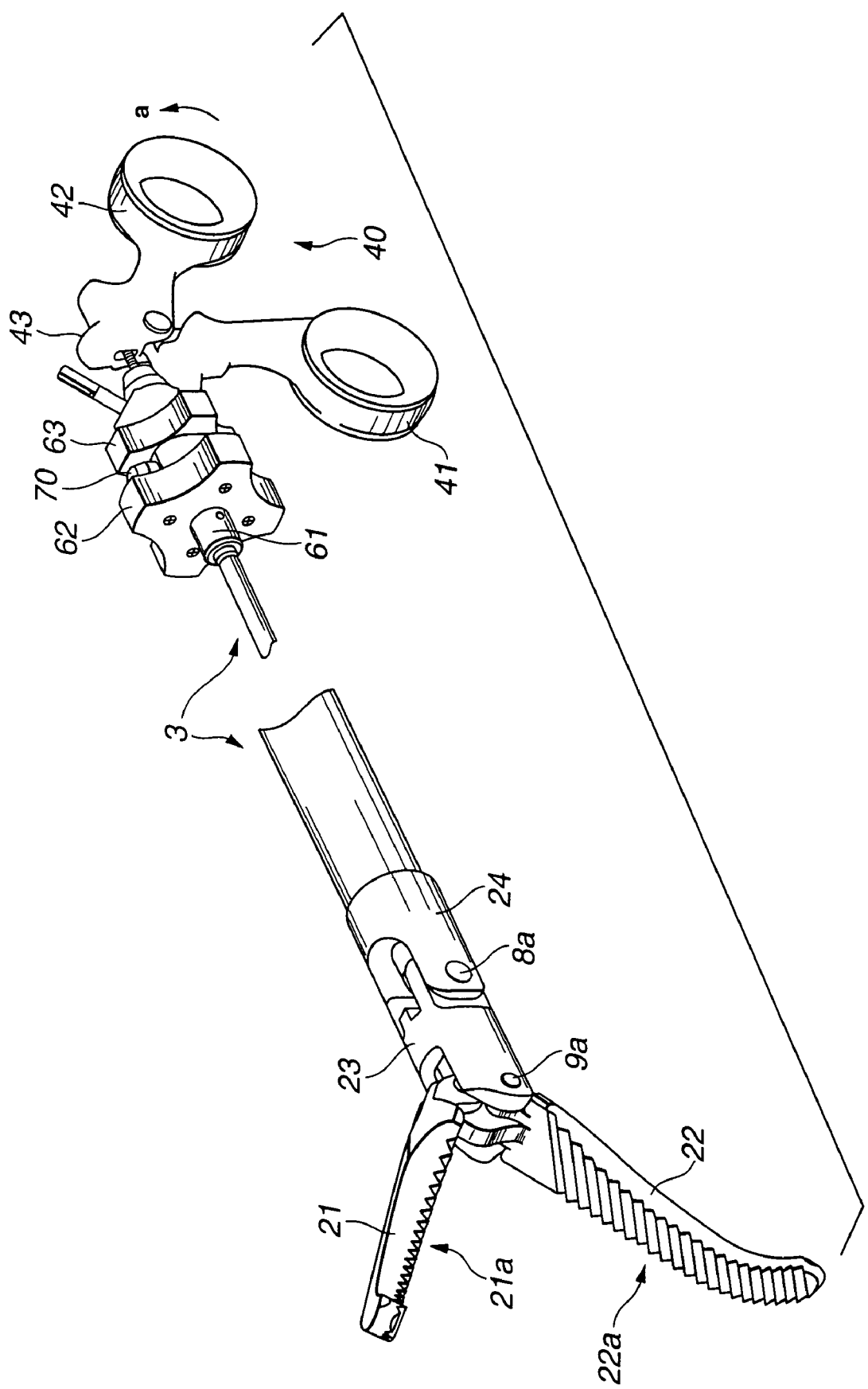
FIG. 11 is a diagram showing an operation of a movable handle of an end effector manipulation portion.
Figure 12:
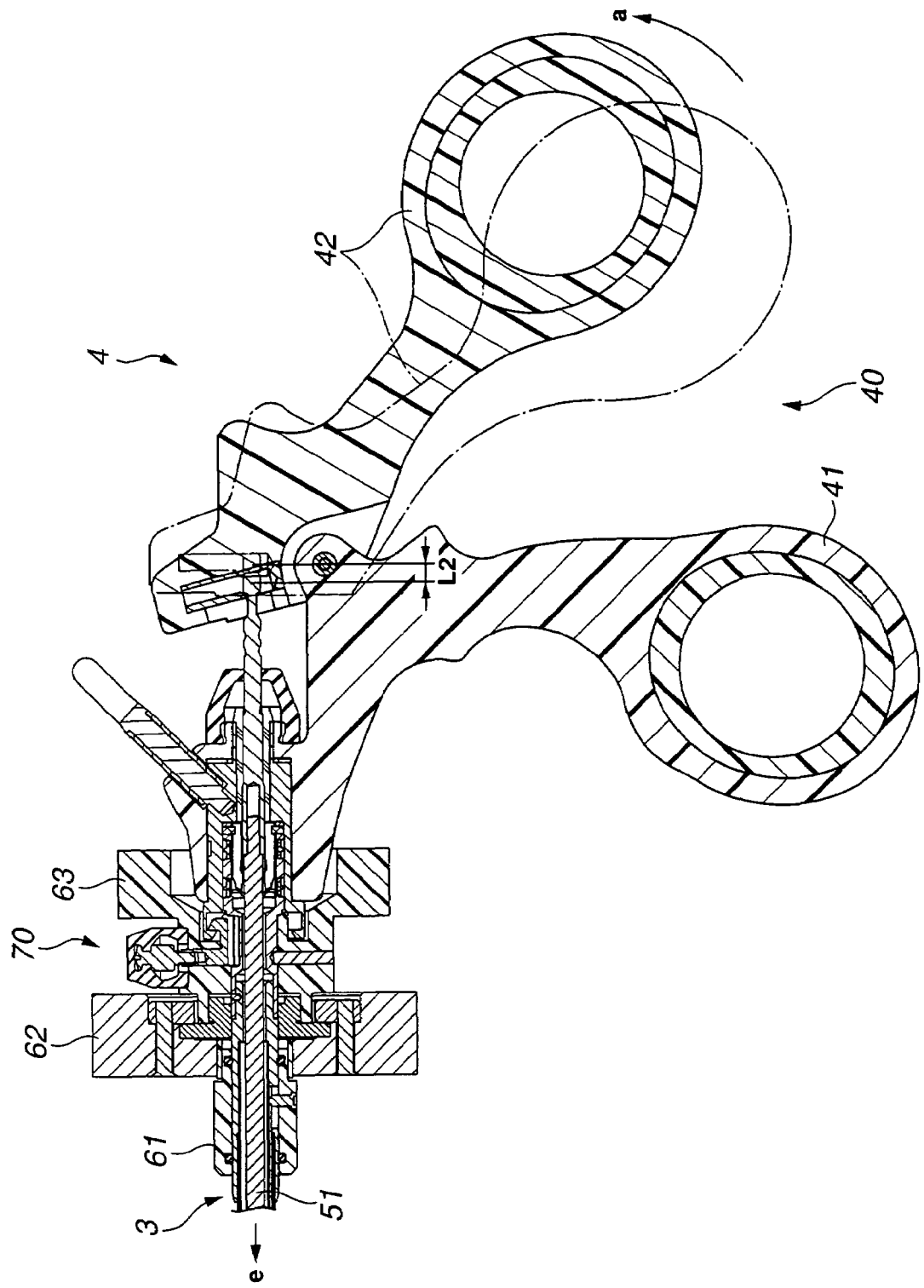
FIG. 12 is a diagram illustrating a manner in which an end effector manipulation rod moves in response to an operation performed on a movable handle.

As shown in FIGS. 3A, 3B, 4A, and 4B, when the end effector 2 is in a non-pivoted position in which the end effector 2 and the insertion portion 3 lie in a straight line, and when the first jaw 21 and the second jaw 22 forming the end effector 2 are in a closed state, if the movable handle 42 is operated such that it pivots on the handle pin 43 in a direction denoted by an arrow a as shown in FIG. 11 or 12 until the movable handle 42 comes to a position represented by solid lines from a position denoted by dashed lines, then the location of the ball 53a of the connecting rod 53 received by the end effector manipulation rod receiving portion 46 changes. Furthermore, the connecting rod 53 moves together with the end effector manipulation rod 51 in a forward direction denoted by an arrow e along the insertion axis. As a result, as shown in FIG. 6, the flat plate-shaped distal end part 51a of the end effector manipulation rod 51 moves forwardly. Thus, the second connection member 26 and the first connection member 25 move forwardly through the end effector base 23. As a result, the first jaw 21 and the second jaw 22 forming the end effector 2 are opened as shown in FIGS. 6, 11, and 13.

Thereafter, if the movable hand 42 is operated so that the ball 53a moves a linear distance L2 along the insertion axis as shown in FIG. 12, the center position of the third connection pin 10c moves a linear distance L2 as shown in FIG. 6. As a result, the first jaw 21 and the second jaw 22 are fully opened to an angle $\theta_2$.

On the other hand, if the movable handle 42 is moved in an opposite direction denoted by an arrow b, the ball 53a and the center position of the third connection pin 10c move backwardly along the insertion axis. As a result, the end effector 2 gradually changes from the opened state into a closed state.

Figure 13:
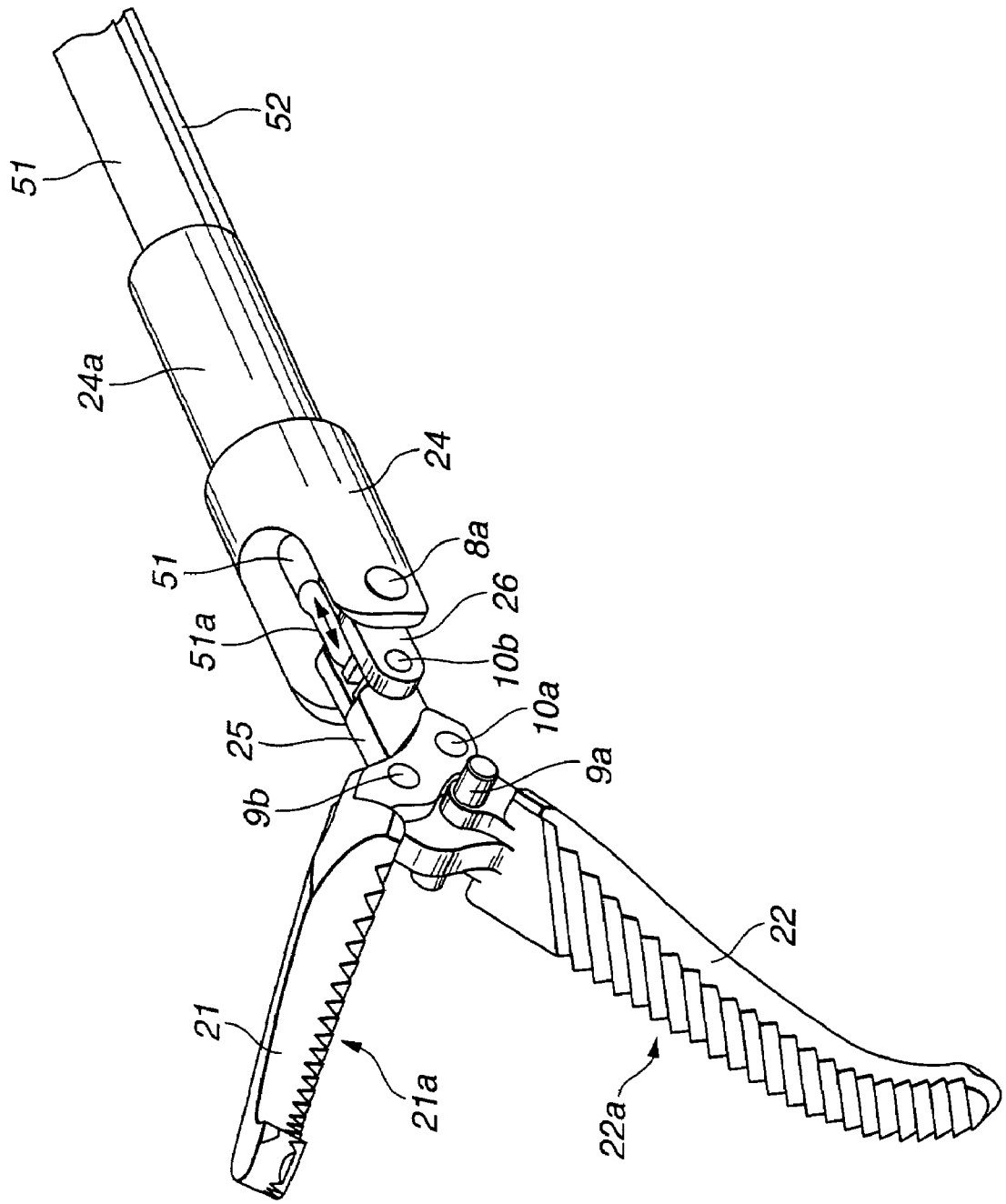
FIG. 13 is a diagram illustrating a manner in which jaws of an end effector are opened or closed in response to motion of a flat plate-shaped distal end part of an end effector manipulation rod, wherein an end effector base is removed to provide an easier understanding.

That is, an operator can open and close the end effector 2 such that the angle between the first jaw 21 and the second jaw 22 changes to a desired value, by properly operating the movable handle 42 thereby moving the flat plate-shaped distal end part 51a forwardly or backwardly as represented by an arrow in FIG. 13.

The pivoting operation using the pivot control knob 62 is described below.

Figure 14:
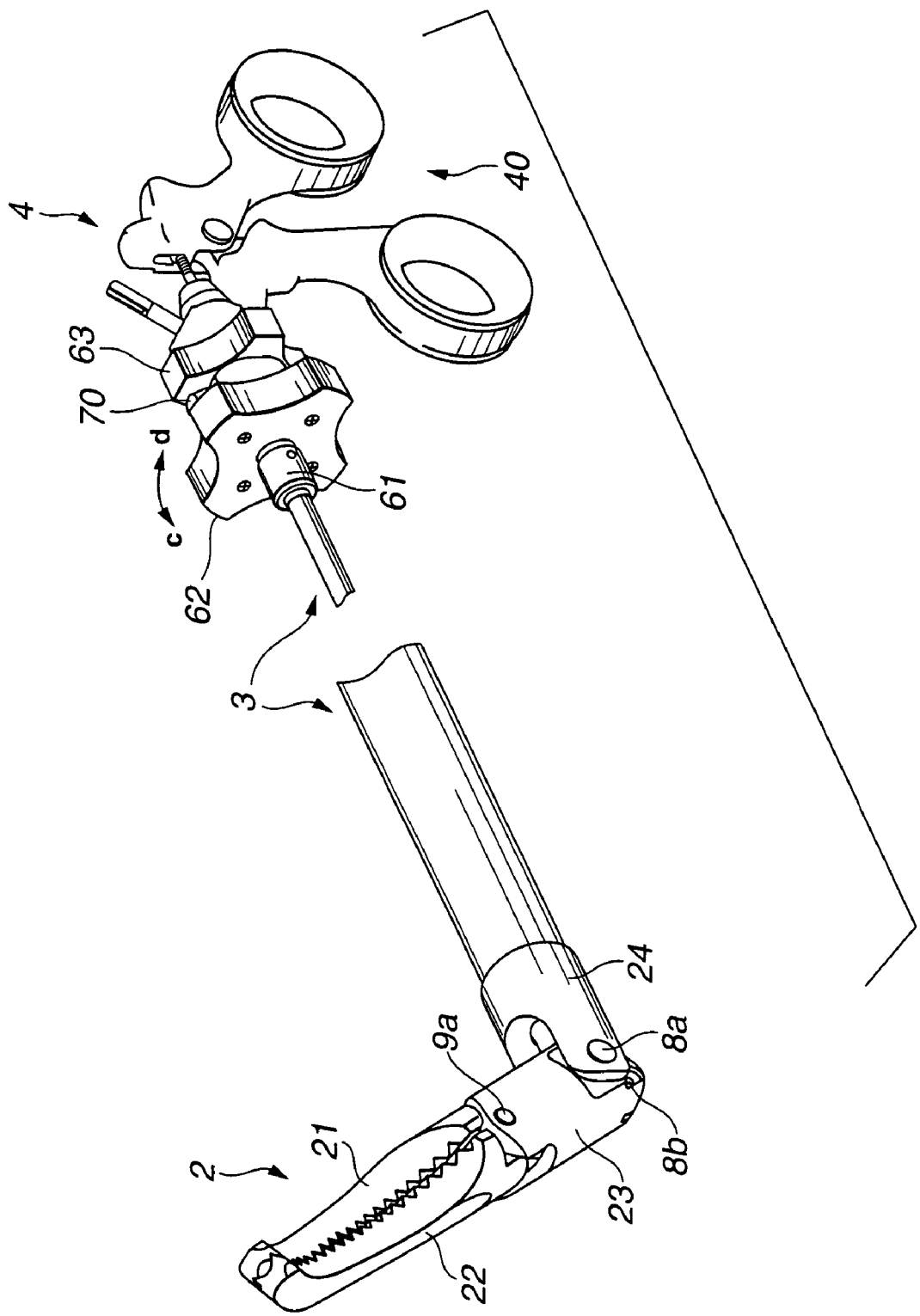
FIG. 14 is a diagram illustrating an operation associated with a pivot control knob.
Figure 15:
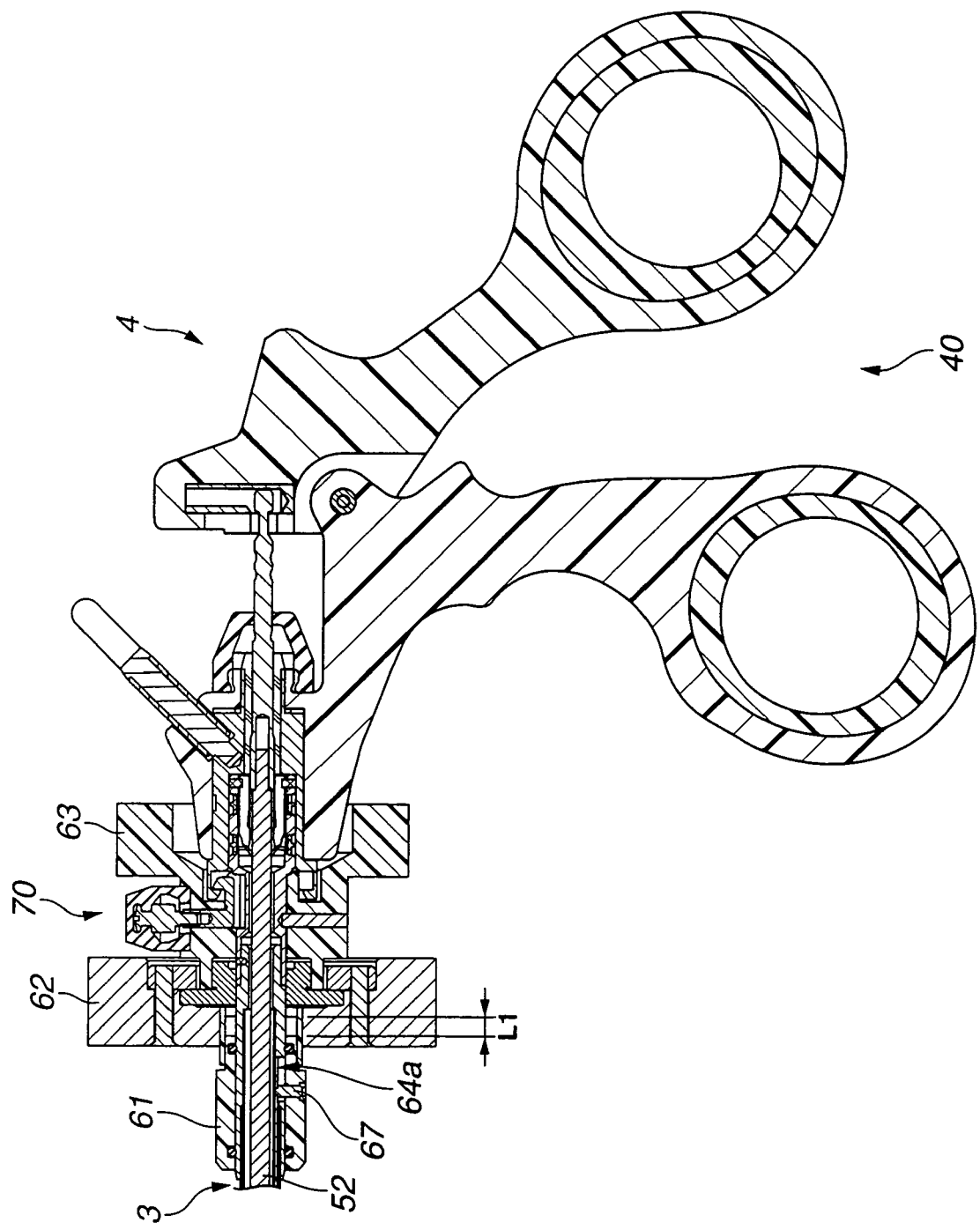
FIG. 15 is a diagram illustrating a manner in which a pivot base and an end effector base manipulation rod move in response to an operation performed on a pivot control knob.

As shown in FIGS. 3A, 3B, 4A, and 4B, when the end effector 2 is in a non-pivoted position in which the end effector 2 and the insertion portion 3 are in a straight line, and when the first jaw 21 and the second jaw 22 forming the end effector 2 are in a closed state, if the pivot control knob 62 is rotated about the insertion axis, for example, in a direction denoted by an arrow d shown in FIG. 14 (or in a direction denoted by an arrow c), the end effector 2 is pivoted as will be described detail below. Note that the pivot control knob 62 can be easily rotated with a finger of one hand with which the end effector manipulation portion 40 is held, because the pivot control knob 62 is disposed closely adjacent, at a distal-end side, to the rotation knob 63 and the pivot control knob 62 is greater in diameter than the rotation knob 63. If the pivot control knob 62 is rotated, the pivot base 61 connected, by means of screwing, with the pivot control knob 62 moves forwardly along the insertion axis by an amount corresponding to the amount by which the pivot control knob 62 is rotated. The motion of the pivot base 61 in the forward direction causes the end effector base manipulation rod 52 integrally fixed by the connection screw 67 with the pivot base 61 to move forwardly, as shown in FIG. 15. As a result, the location of the connection screw 67 changes within the long hole 64a.

Figure 16:
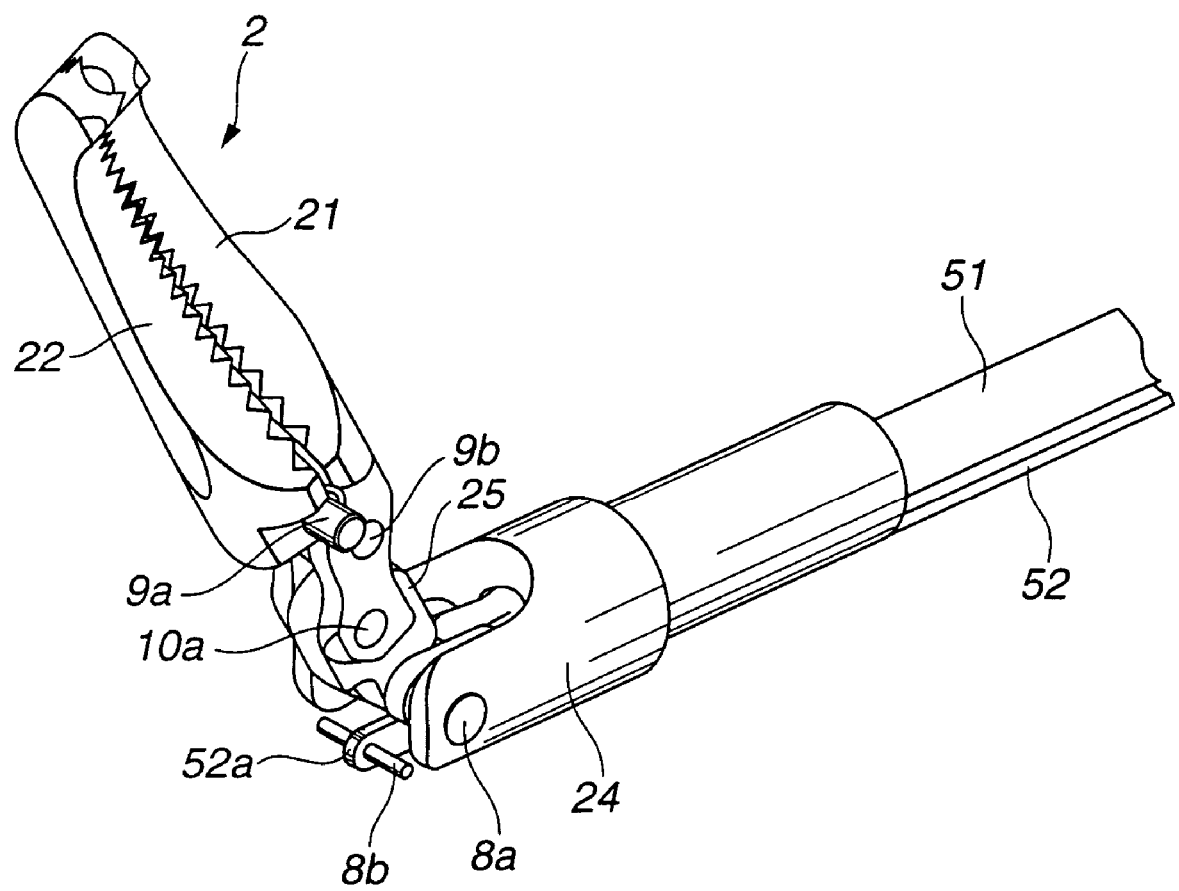
FIG. 16 is a diagram illustrating the relationship between the motion of an end effector and the motion of a distal end unit of an end effector base manipulation rod, wherein an end effector base is removed to provide an easier understanding.

The motion of the end effector base manipulation rod 52 in the forward direction causes the distal end unit 52a to move forwardly as shown in FIG. 16. As a result, the second pivot pin 8b moves forwardly, and thus the end effector base 23, on which the first jaw 21 and the second jaw 22 are disposed, pivots on the first pivot pin 8a. Thus, the pivot angle gradually changes.

If the pivot base 61 is moved a linear distance $L_1$ along the insertion axis by rotating the pivot control knob 62 as shown in FIG. 15, the center position of the second pivot pin 8b moves a linear distance $L_1$ as shown in FIG. 5. As a result, the end effector 2 pivots from a horizontal position denoted by dashed lines to a fully pivoted position at an angle of $\theta_1$.

In this state, the center of the second connection pin 10b is coincident with the center of the first pivot pin 8a on which the end effector base 23 pivots. This allows the first jaw 21 and the second jaw 22 to be maintained in the closed state when the end effector base 23 pivots.

A pivoting operation using a combination of the pivot control knob 62 and the movable handle 42 is described below.

Figure 17:
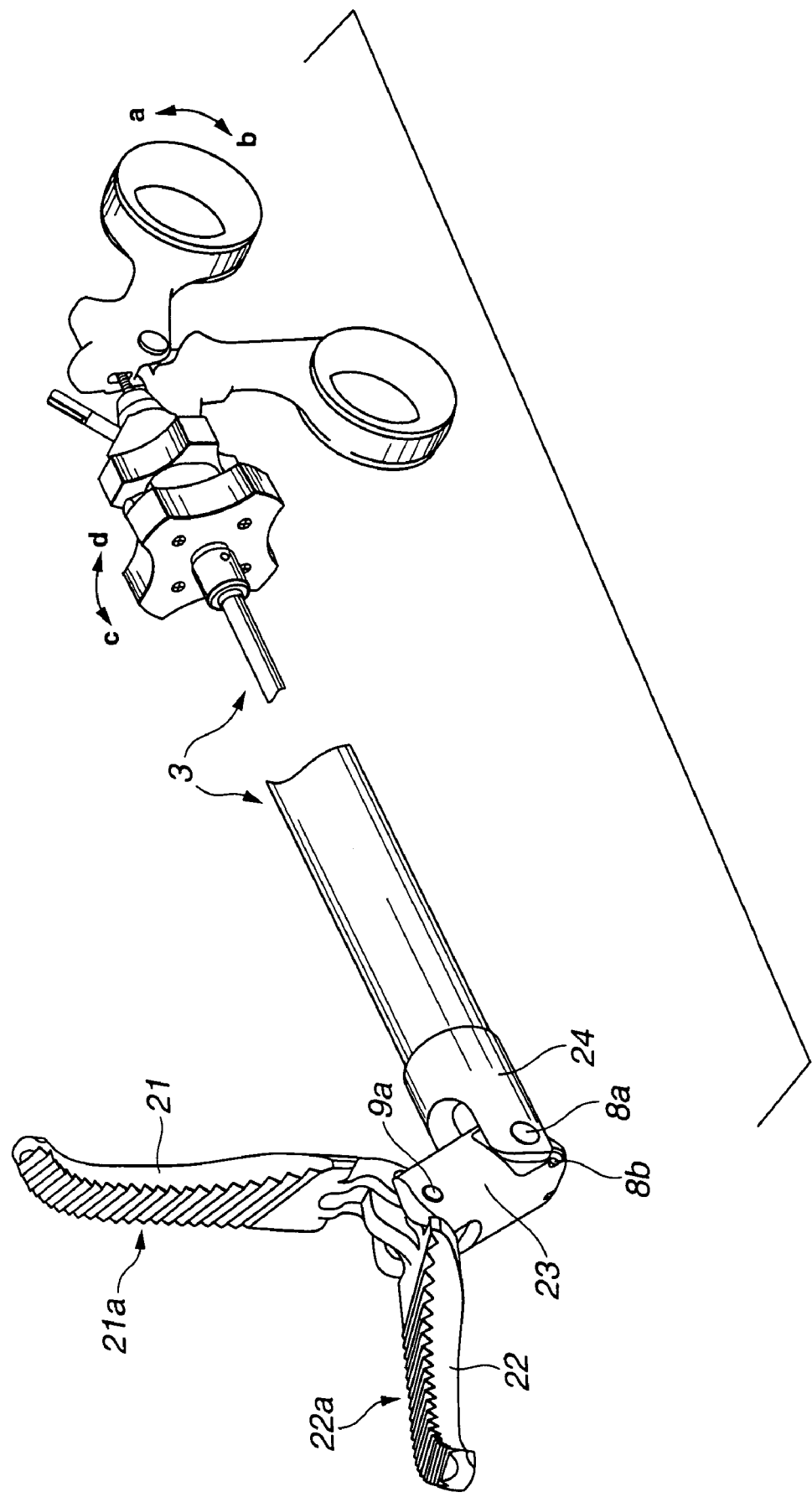
FIG. 17 is a diagram illustrating an operation of a movable handle of an end effector manipulation portion in a state in which a pivot control knob is operated.
Figure 18:
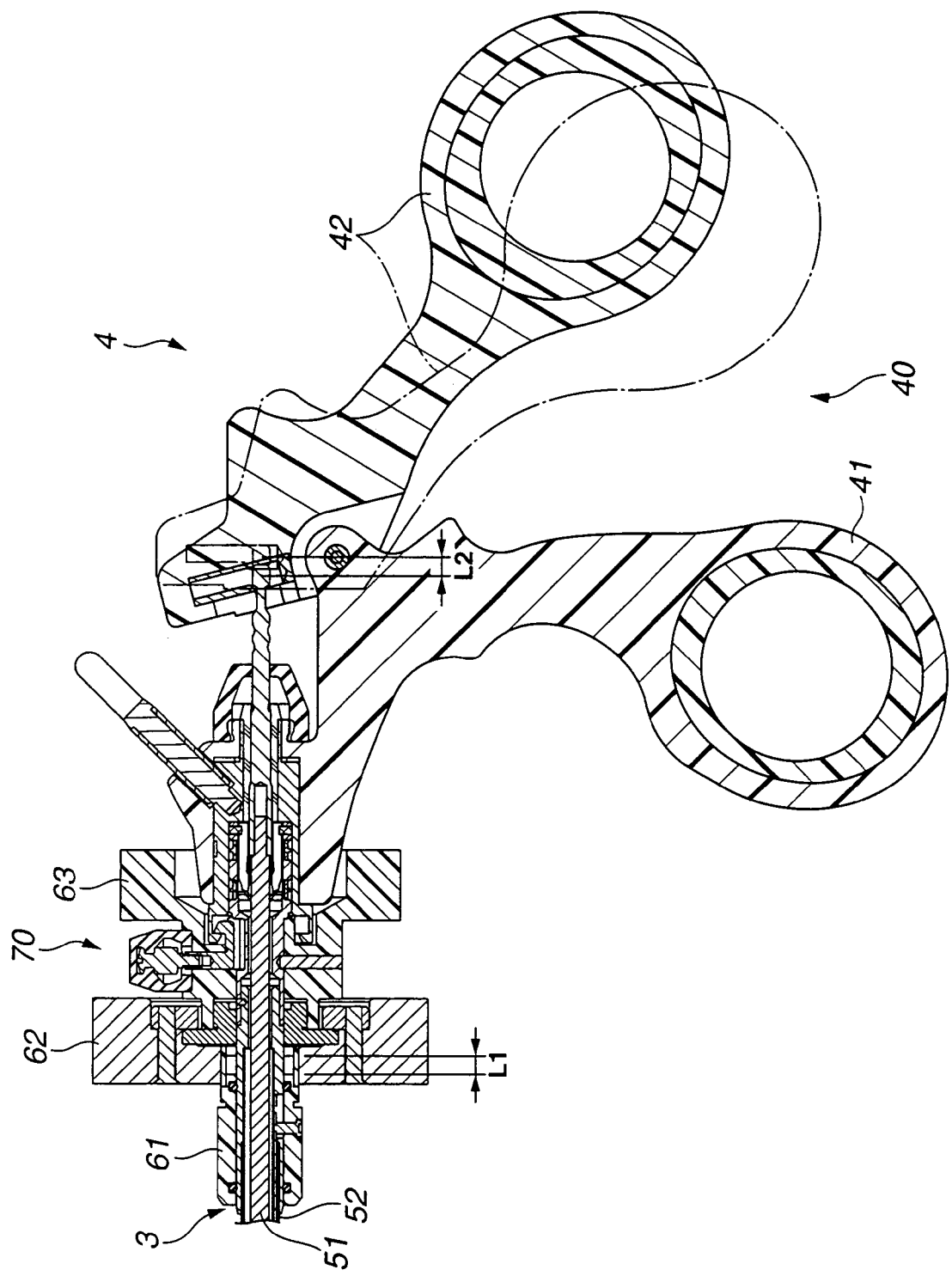
FIG. 18 is a diagram illustrating a manner in which a pivot base and an end effector base manipulation rod move in response to an operation performed on a pivot control knob, and also illustrating a manner in which an end effector manipulation rod moves in response to an operation performed on a movable handle.
Figure 19:
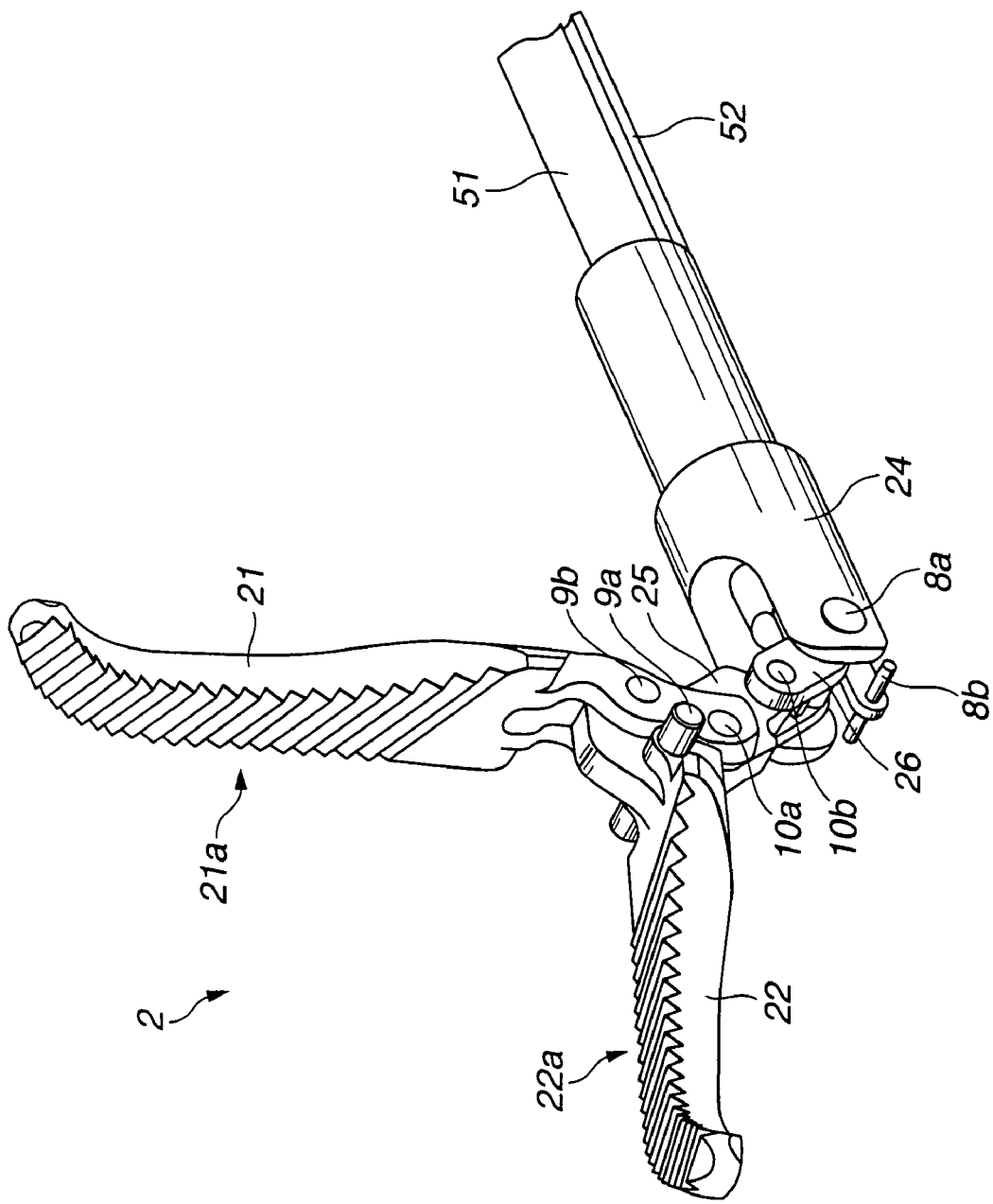
FIG. 19 is a diagram illustrating a manner in which jaws of an end effector are opened or closed when the end effector is in a pivoted state.

For example, as shown in FIGS. 17 and 18, if the end effector 2 is moved into the pivoted position as shown in FIG. 14 by rotating the pivot control knob 62, and the movable handle 42 is then moved in a direction denoted by an arrow a as shown in FIG. 17 or 18, then, as shown in FIG. 7, the flat plate-shaped distal end part 51a of the end effector manipulation rod 51 moves from a position represented by dashed lines to a position represented by solid lines. As a result, the second connection member 26 and the first connection member 25 move forwardly in the end effector base 23. This causes the first jaw 21 and the second jaw 22 forming the end effector 2 to open as shown in FIG. 17 and 19.

In this state, the center of the third connection pin 10c is coincident with the center of the first pivot pin 8a on which the end effector base 23 pivots. This allows the first jaw 21 and the second jaw 22 to be maintained in the open state when the end effector base 23 pivots.

That is, in a state in which the end effector 2 has been pivoted into a desired position by properly moving the pivot base 61, the first jaw 21 and the second jaw 22 can be opened or closed by operating the movable handle 42. In the combinational operation of pivoting of the end effector 2 and opening/closing of the first jaw 21 and the second jaw 22 of the end effector 2, pivoting and opening/closing can be performed by desired arbitrary amounts.

Figure 20:
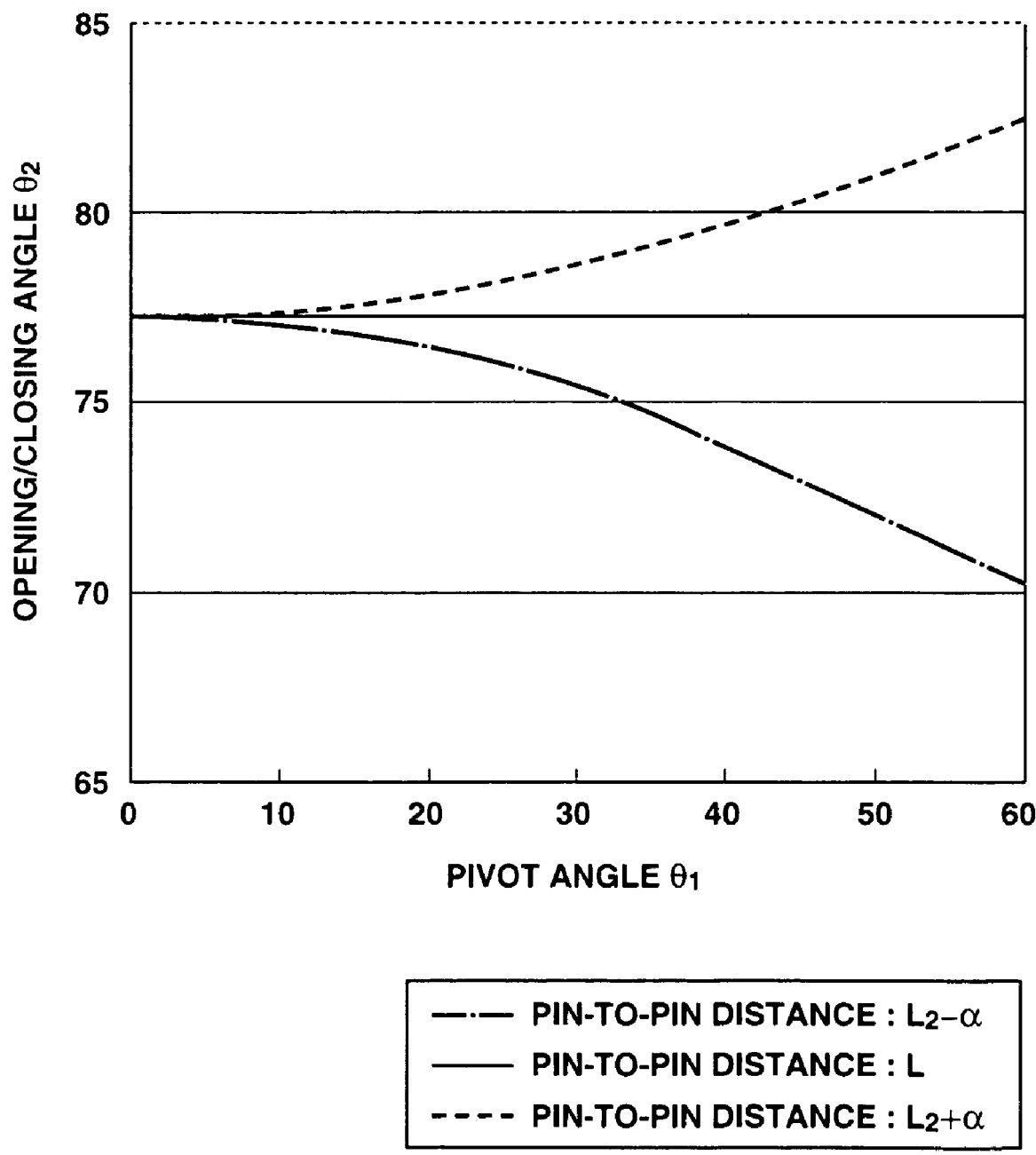
FIG. 20 is a diagram illustrating the relationships among the pin-to-pin distance, the pivot angle $\theta_1$, and the opening angle $\theta_2$.

Referring to FIG. 20, the relationships among the pin-to-pin distance of the second connection member 26, the pivoting angle $\theta_1$, and the opening angle $\theta_2$ are described below.

In FIG. 20, a solid line indicates the opening angle $\theta_2$ when the pin-to-pin distance between the second connection pin 10b and the third connection pin 10c is maintained at L2. A dashed line indicates the opening angle $\theta_2$ for a pin-to-pin distance smaller than L2. A broken line indicates the opening angle $\theta_2$ for a pin-to-pin distance greater than L2.

When the pin-to-pin distance is smaller than L2, the angle between the first jaw 21 and the second jaw 22 decreases as the pivoting angle of the end effector 2 increases starting from the straight position, as indicated by the dashed line. On the other hand, when the pin-to-pin distance is greater than L2, the angle between the first jaw 21 and the second jaw 22 increases as the pivoting angle of the end effector 2 increases starting from the straight position, as indicated by the broken line. That is, in any case, the angle between the jaws changes with the pivoting angle.

In the present embodiment, to avoid the above problem, the structure is designed such that when the flat plate-shaped distal end part 51a of the end effector manipulation rod 51 moves by L2, the first jaw 21 and the second jaw 22 are fully opened, and the pin-to-pin distance equals to L2. Thus, when the first jaw 21 and the second jaw 22 are in the closed state, the center of the second connection pin 10b is coincident with the center of the first pivot pin 8a, while the center of the third connection pin 10c is coincident with the center of the first pivot pin 8a when the first jaw 21 and the second jaw 22 are in the open state. Thus, in the present embodiment, when the end effector 2 is pivoted to any angle within a particular range, for example, from 0° to 60°, the angle between the first jaw 21 and the second jaw 22 is maintained constant as indicated by the solid line in FIG. 20.

Now, the operation of the rotation knob 63 is described below.

If the rotation knob 63 is rotated about the insertion axis, the second base tube 65, the first base tube 64, the first channel 33, and the second channel 34, which are integrally connected with the rotation knob 63, rotate about the insertion axis. Simultaneously with the above rotation, the end effector manipulation rod receiving portion 46 including the guide 46a receiving the rotation guide pin 65a causes the end effector manipulation rod 51 integrally connected with the connection rod 53, whose smooth side faces 53b are in contact with the end effector manipulation rod receiving portion 46, to rotate about the insertion axis. That is, the insertion portion 3 as a whole can be rotated about the insertion axis to arbitrarily change the direction of the plane in which the first jaw 21 and the second jaw 22 are opened and closed.

The insertion portion assembly 6 and the manipulation portion assembly 7 are integrally connected by engaging the locking hook 71a of the first management member 71 forming the release button 70 with the management part 45a of the attaching portion 45. Thus, if the first management member 71 is moved toward the center of the insertion axis while pressing down the button 73 of the release button 70, the engagement between the locking hook 71a and the management part 45a is released. In this released state, if the movable handle 42 is pivoted on the handle pin 43 and simultaneously the end effector manipulation rod 51 is moved, the ball 53a of the connecting rod 53 is removed from the end effector manipulation rod receiving portion 46. As a result, the insertion portion assembly 6 and the manipulation portion assembly 7 are separated from each other.

If the connection screw 67 on the pivot base 61 is released, it becomes possible to remove the end effector base manipulation rod 52 from the pivot base 61. In this state, if the end effector manipulation rod 51 and the end effector base manipulation rod 52 are removed from the first channel 33 and the second channel 34, respectively, the insertion portion assembly 6 and the end effector assembly 5 are separated from each other.

As described above, in the surgical instrument according to the present embodiment, the pivot control knob for pivoting the end effector and the end effector manipulation portion having the movable handle for manipulating the end effector connected, via the link mechanism including the joint, with the distal end of the end effector manipulation rod are disposed such that the range within which the end effector manipulation rod is moved forwardly or backwardly by the movable handle is set to a particular value and furthermore the pin-to-pin distance between the third connection pin and the second connection pin engaged with the second connection member is set to a particular value such that when the end effector manipulation rod is moved from the first end position to the second end position, the relative position between the connection pins and pivot pins changes from a relative position in which the central axis of the second connection pin and the central axis of the first pivot pin 8a are coincident with each other to a relative position in which the central axis of the third connection pin and the central axis of the first pivot 8a are coincident with each other, thereby ensuring that an operator can manipulate the end effector in a desired manner regardless of the pivoting state of the end effector.

Furthermore, in the surgical instrument according to the present embodiment, the pivot control knob for pivoting the end effector and the end effector manipulation portion having the movable handle for opening and closing the first jaw and the second jaw forming the end effector are provided such that the end effector base manipulation rod for transmitting the operation of the pivot control knob to the end effector and the end effector manipulation rod for transmitting the operation of the movable handle to the end effector are both made of a rigid material thereby ensuring that when an operator operates the pivot control knob or the movable handle, the end effector is pivoted or opened/closed in exactly the same manner as intended by the operator.

Use of the rigid material allows the end effector base manipulation rod and the end effector manipulation rod to move without encountering deformation even when an external force is applied to the end effector. Thus, it is ensured that pivoting of the end effector and opening/closing of the jaws of the end effector can be performed precisely.

Furthermore, connecting the end effector, the pivot control knob, and the movable handle using rigid connection members makes it possible for an operator to operate the pivot control knob or the movable handle while perceiving a force applied to fingers of a hand by which the pivot control knob or the movable handle is operated wherein the force applied to the fingers exactly correspond to an external force applied to the end effector. More specifically, when a body tissue is grasped between the grasping surfaces having protrusions and depressions formed thereon by closing the jaws of the end effectors, an operator can perceive a reaction force from the body issue. The perception of the reaction force ensures that the operator can precisely grasp the body tissue and also ensures that the operator can dissect a body tissue by opening the jaws.

In the surgical instrument according to the present embodiment, in addition to the end effector manipulation portion for operating the end effector, the pivot control knob for pivoting the end effector and the second rotation knob for rotating the end effector and the insertion portion as a whole about the insertion axis are formed such that the pivot control knob has an external diameter greater than the external diameter of the second rotation knob, and those two knobs are placed such that they are located close to each other and such that the second rotation knob is located at a side closer to the end effector manipulation portion thereby making it possible for an operator to easily rotate the pivot control knob or the rotation knob with a finger of a hand by which the end effector manipulation portion is held.

This makes it possible to operate the surgical instrument with fingers of one hand by which the end effector manipulation portion is held, without using a finger of the other hand. This allows another treatment tool or the like to be operated with another hand of the operator. Furthermore, the second rotation knob located close to the fixed handle can be operated or held with, for example, the index finger, and the pivot control knob located farther from the fixed handle can be operated or held with the middle finger.

In the present embodiment, because the surgical instrument can be separated into the treatment portion assemble, the insertion portion assembly, and the manipulation portion assembly, the surgical instrument can be easily cleaned in a short time after using the surgical instrument.

Figure 21:
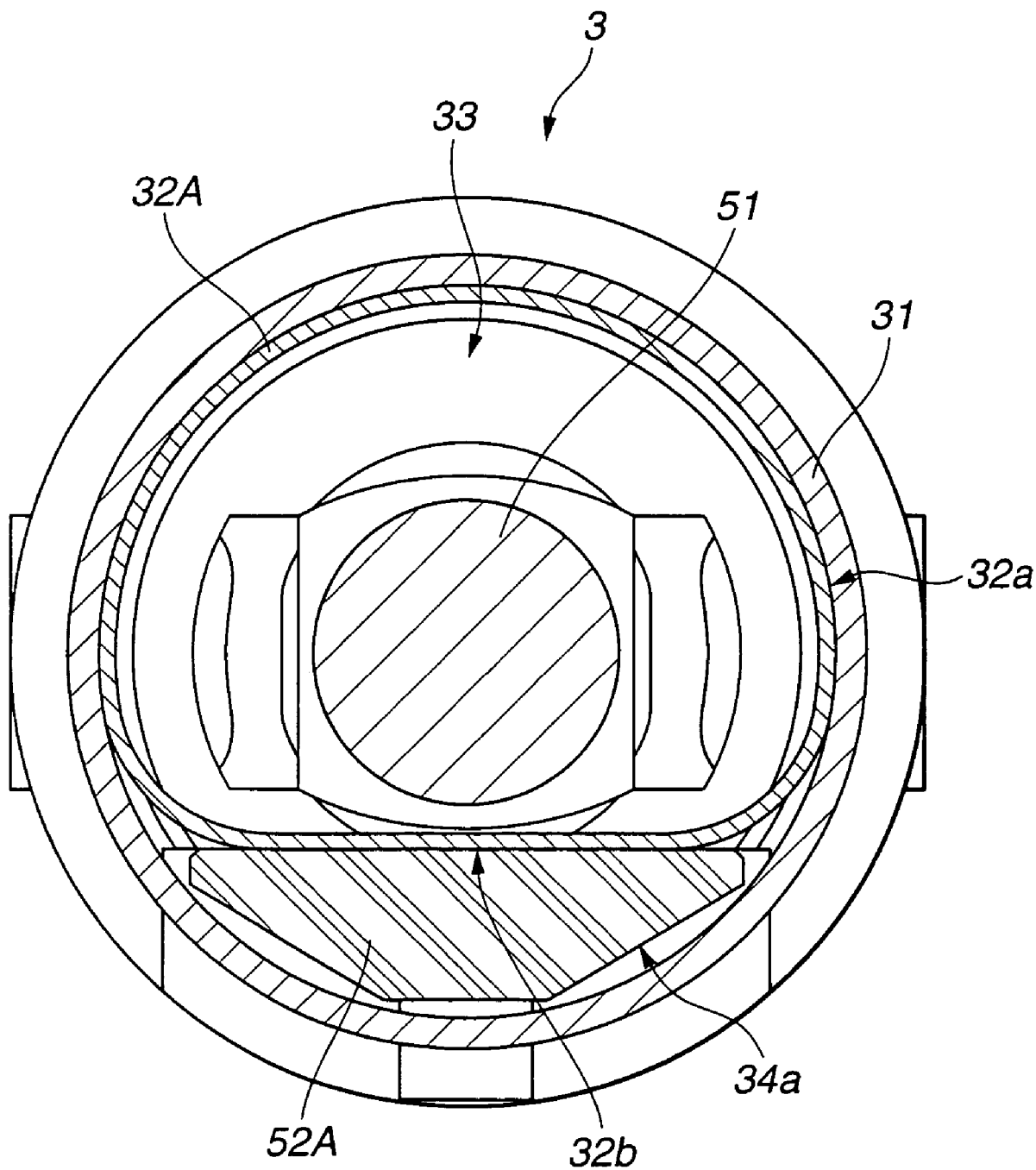
FIG. 21 is a diagram illustrating the structure of an end effector manipulation rod and the structure of an insertion portion having a cross-sectional area substantially equal to that of the end effector manipulation rod.

The cross-sectional shape of the end effector base manipulation rod inserted through the second channel is not limited to a rectangle. For example, as shown in FIG. 21, to change the external size of the inner tube 32A disposed in the inside of the insertion tube 31, for example, the flat part 32*b* may be formed so as to be rather long such that the second channel 34*a* has a greater cross-sectional area so that the end effector base manipulation rod 52A has a cross-sectional area substantially equal to the cross-sectional area of the end effector manipulation rod 51.

As described above, if the external shape of the inner tube disposed in the insertion tube of the insertion portion is properly set such that the end effector manipulation rod and the end effector base manipulation rod are allowed to be equal in cross-sectional area thereby preventing, in a more reliable manner, a trouble from occurring due to bending of the end effector manipulation rod or the end effector base manipulation rod. Furthermore, this ensures that the end effector is prevented from returning to its straight position against the intention of an operator in the middle of a pivoting or opening/closing operation.

Figure 22:
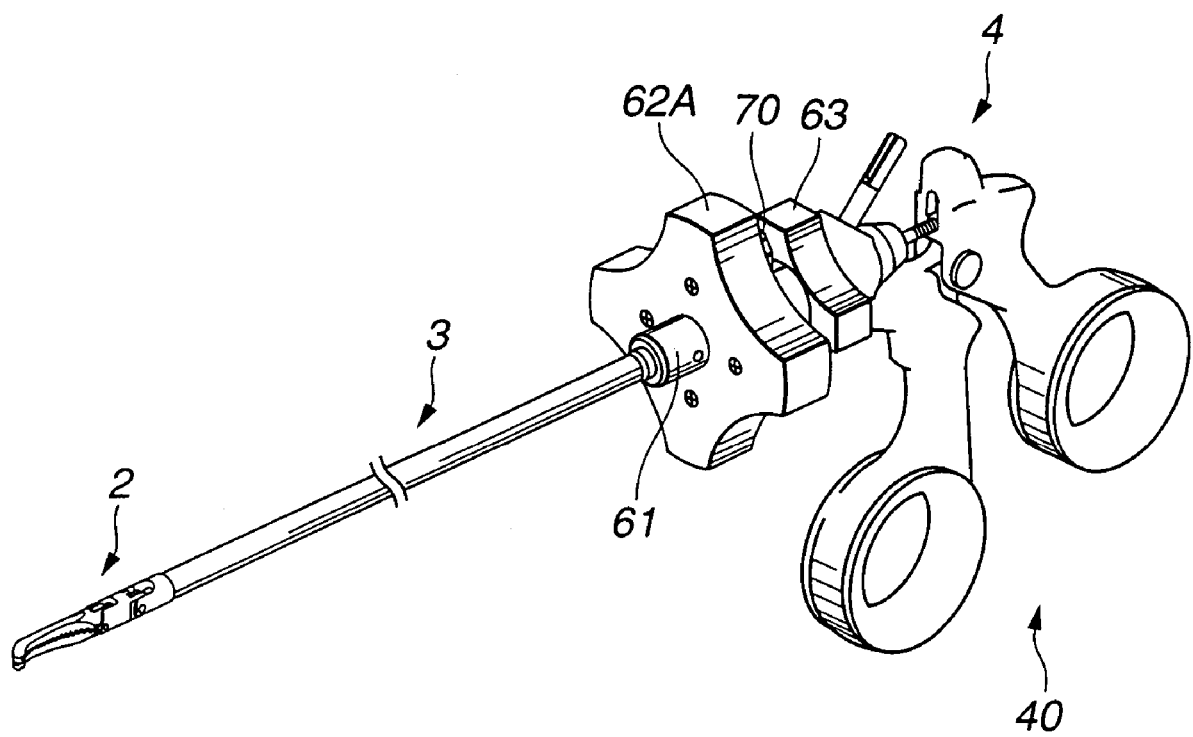
FIG. 22 is a diagram illustrating a surgical instrument including a pivot control knob with a further increased diameter.

Although in the present embodiment, the pivot control knob 62 is formed such that the external diameter thereof is 1.2 times greater than the diameter of the rotation knob 63, the external diameter of the pivot control knob 62A may be set, for example, to be 1.5 times greater than the diameter of the rotation knob 63 as shown in FIG. 22. However, to achieve a good balance without increasing the weight of the surgical instrument and to achieve high operability and high grasping performance, it is desirable that the external diameter of the pivot control knob be set to be less than 2 times the external diameter of the rotation knob.

The greater external diameter of the pivot control knob makes it possible to more easily operate the pivot control knob with a finger of a hand by which the grasp control portion is held, the greater external diameter of the pivot control knob also results in an increase in moment that allows the pivot control knob to be rotated by a smaller force.

Now, referring to FIGS. 23A to 25, a second embodiment of the present invention is described below.

Figure 23A:
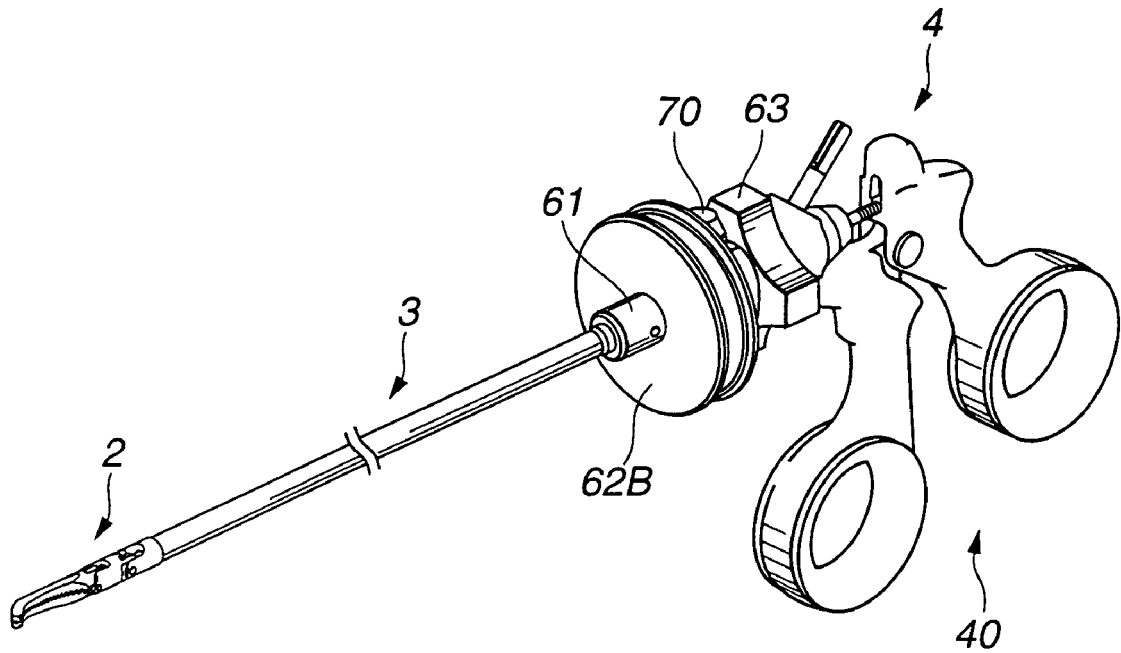
FIG. 23A is a diagram illustrating a surgical instrument whose end effector is in a position in which the end effector and an insertion portion lie in a straight line.
Figure 23B:
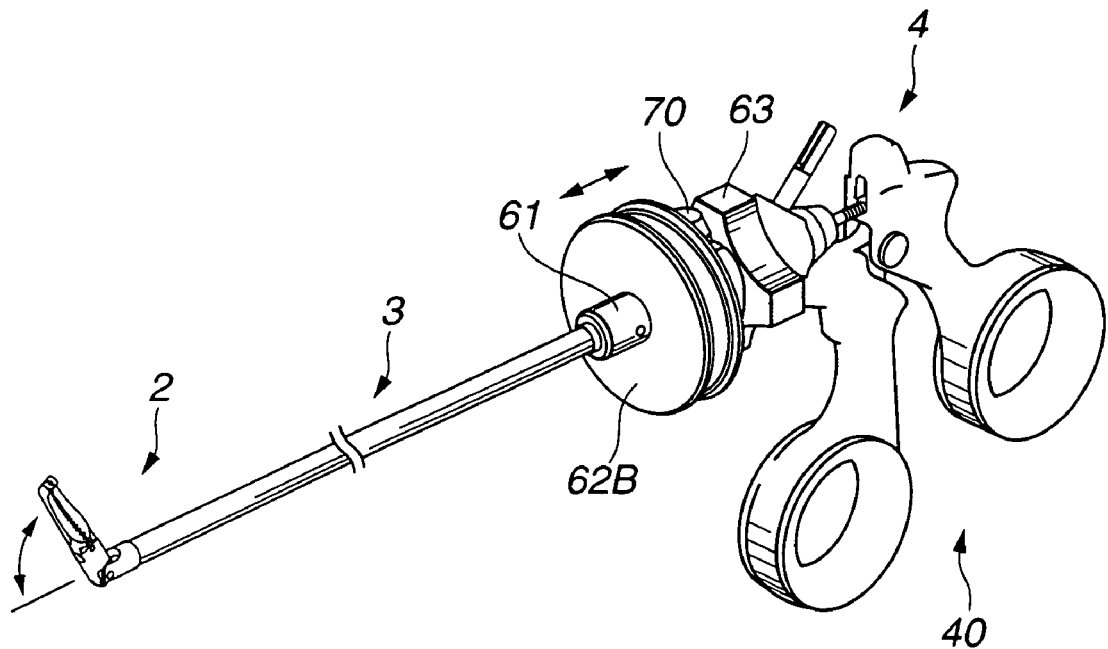
FIG. 23B is a diagram illustrating the surgical instrument whose end effector is in a fully pivoted position.

As shown in FIGS. 23A and 23B, in the surgical instrument 1 according to the second embodiment, the second operation control portion is in the form of a backward/forward-moving knob 62B that moves forwardly and backwardly along the axis of the insertion portion 3. When the backward/forward-moving knob 62B is moved to a location closest to the fixed handle, the end effector comes into a position in which the end effector and the insertion portion lie in a straight line as shown in FIG. 23A. When the backward/forward-moving knob 62B is moved to a location farthest away from the fixed handle, the end effector comes into a fully pivoted position as shown in FIG. 23B.

Figure 24:
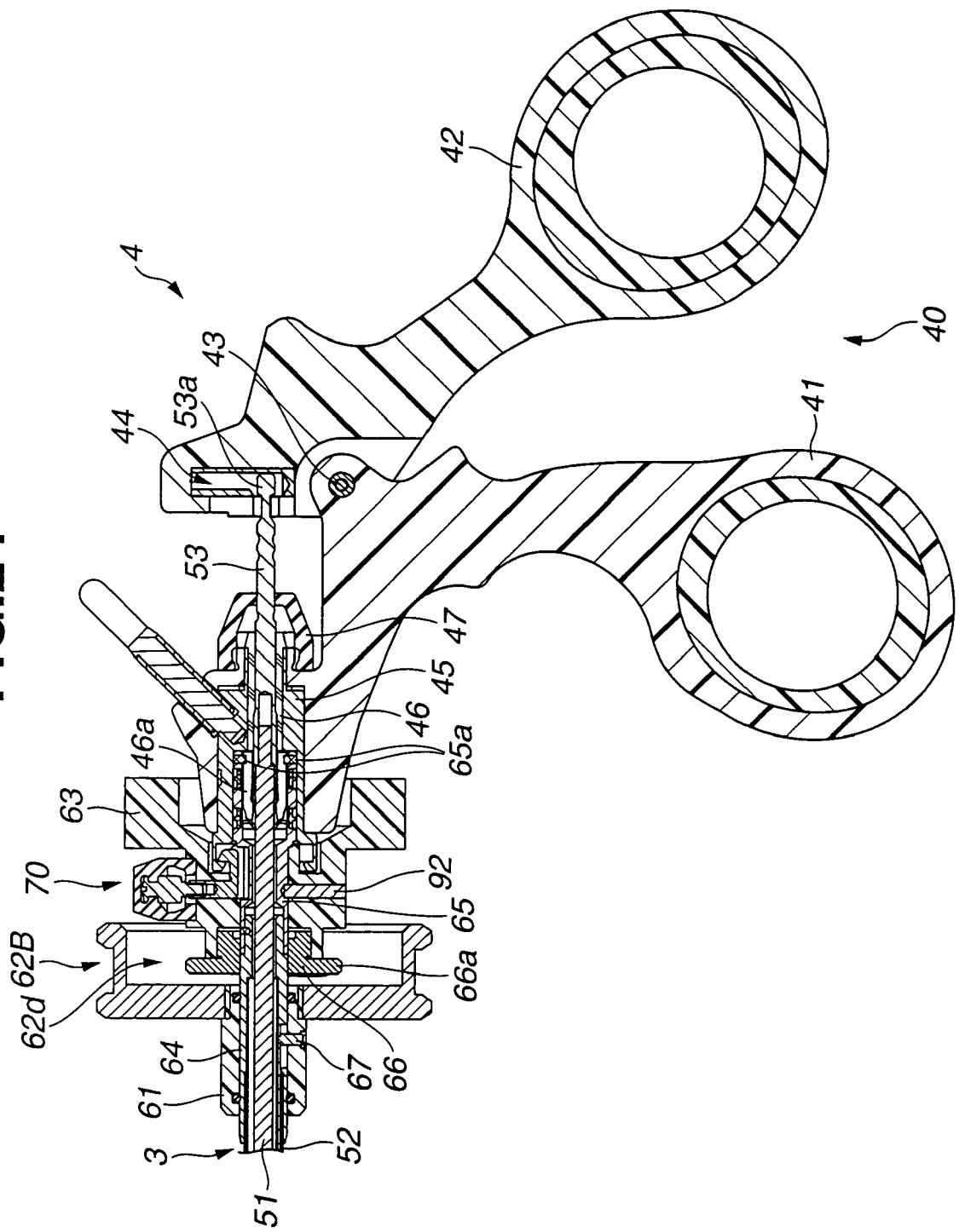
FIG. 24 is a cross-sectional view illustrating an insertion portion assembly and a manipulation portion assembly in a state in which the end effector is in the pivoted position shown in FIG. 23A.
Figure 25:
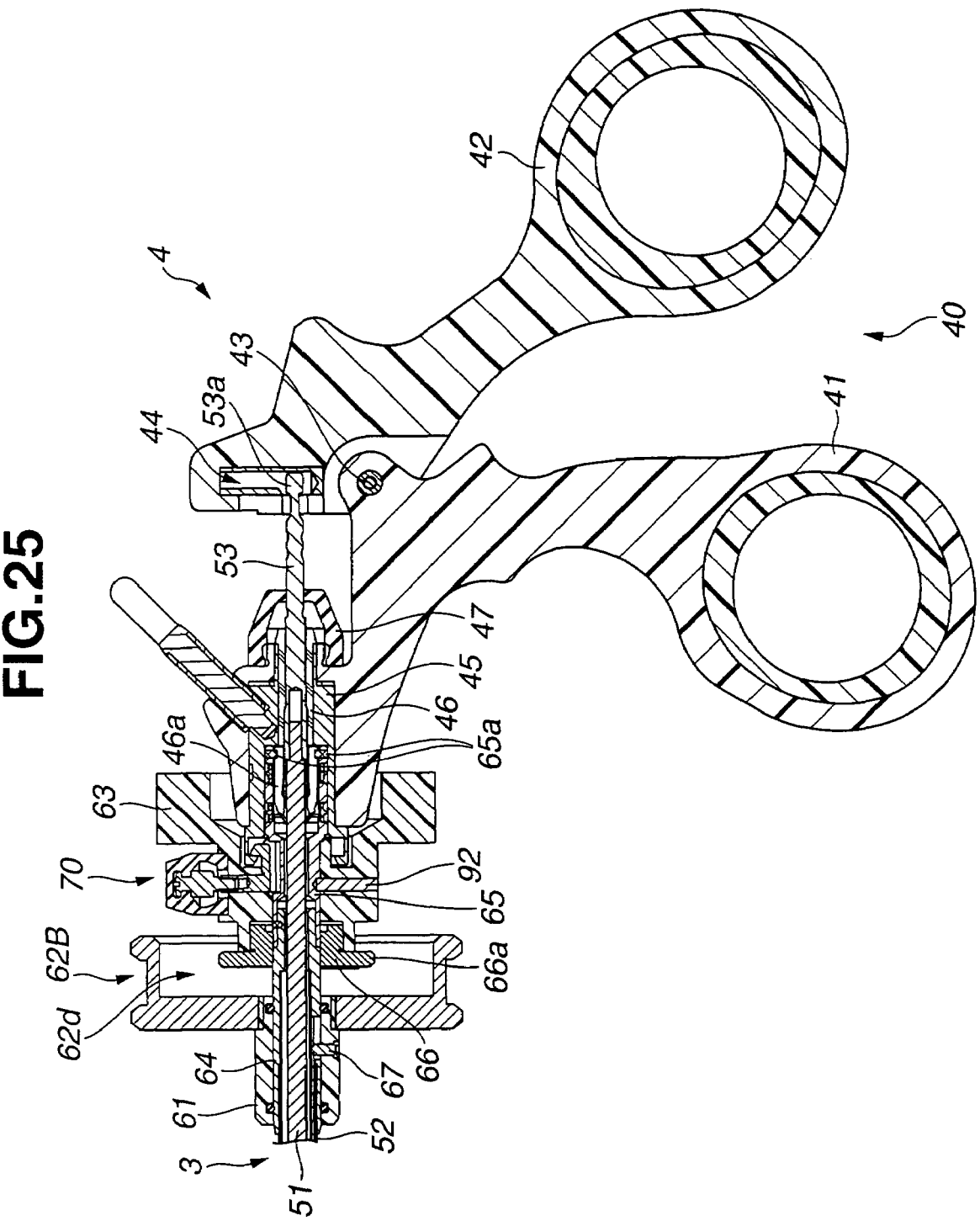
FIG. 25 is a cross-sectional view illustrating the insertion portion assembly and the manipulation portion assembly in a state in which the end effector is in the pivoted position shown in FIG. 23B.

In the present embodiment, as shown in FIGS. 24 and 25, the backward/forward-moving knob 62B is formed in the shape of a barrel having a hollow 62*d*. In this hollow 62*d*, a flange 66*a* is disposed. The backward/forward-moving knob 62B and the pivot base 61 are integrally fixed to each other by means of screwing.

In this structure, if the backward/forward-moving knob 62B is moved forwardly or backwardly along the axis of the insertion portion as indicated by an arrow in FIG. 23B, the pivot base 61 integrally connected with the backward/forward-moving knob 62B moves to a location shown in FIG. 24 or 25. As a result, the end effector base manipulation rod 52 integrally connected, by the connection screw 67, with the pivot base 61 moves forwardly or backwardly in an axial direction.

The external diameter of the backward/forward-moving knob 62B is set to be 1.2 times greater than that of the rotation knob 63. The structures and the operations of the other portions are similar to those according to the first embodiment, and those similar members, denoted by similar reference numerals to those in the first embodiment, are not described in further detail herein.

In the present embodiment, as described above, the surgical instrument includes the end effector manipulation portion for operating the end effector, the rotation knob for rotating the end effector and the insertion portion as a whole about the axis of insertion axis, and also the pivot control knob that is formed so as to have an external diameter greater than the external diameter of the rotation knob and that is located close to the rotation knob such that the pivot control knob can move toward and away from the end effector thereby making it possible to easily operate the pivot control knob and the rotation knob with a finger of one hand by which the end effector manipulation portion is held.

Figure 26:
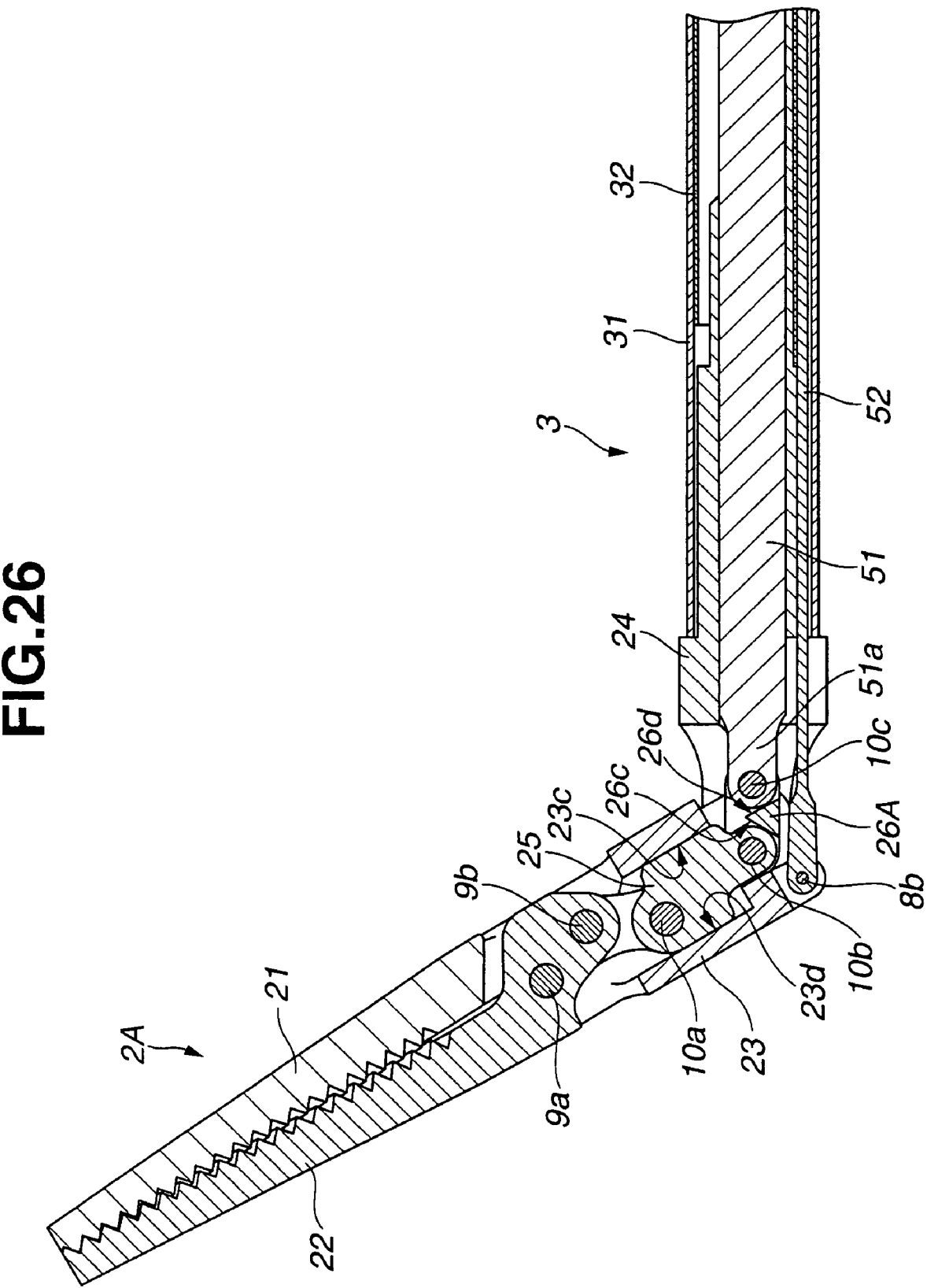
FIG. 26 is a diagram illustrating a surgical instrument in a state in which an end effector including a second connection member having a characteristic structure is in a pivoted position and the respective pair of jaws of the end effector are closed.
Figure 27:
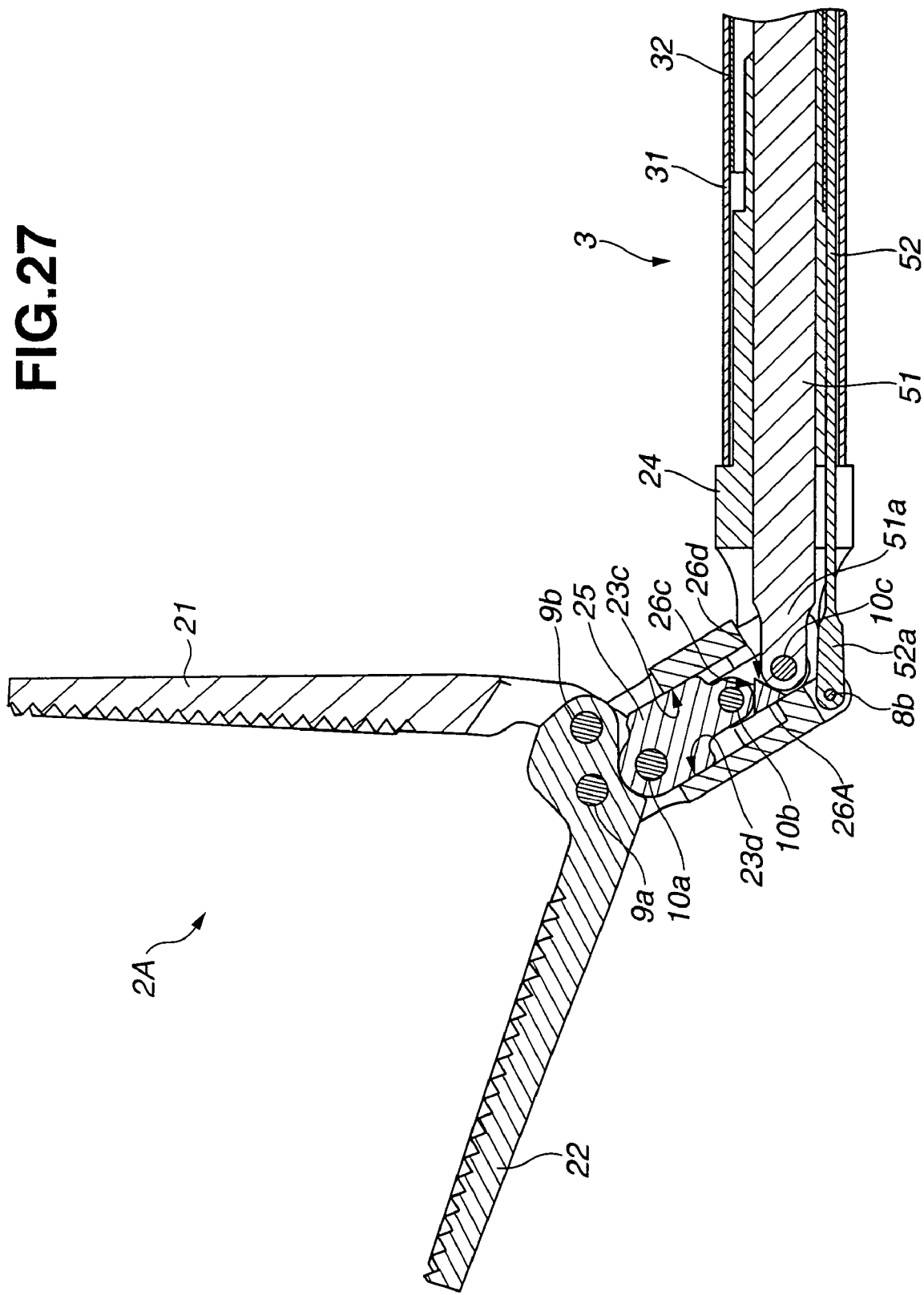
FIG. 27 is a diagram illustrating a surgical instrument in a state in which an end effector including a second connection member having a characteristic structure is in a pivoted position and a pair of jaws of the end effector is opened.

Referring to FIGS. 26 and 27, a third embodiment of the present invention is described below.

As shown in FIGS. 26 and 27, in the surgical instrument 1 according to the present embodiment, a first slanting contact surface 26c and a second slanting contact surface 26d are provided in the center of the second connection member 26A. Accordingly, the end face of the proximal end part of the first connection member 25 is in contact with the first slanting contact surface 26c. The head-side end face of the flat plate-shaped distal end part 51a disposed on the distal end of the end effector manipulation rod 51 is in contact with the second slanting contact surface 26d.

When the end effector 2A is in a pivoted position, if the end effector manipulation rod 51 is moved forwardly to push up the first connection member 25 via the second connection member 26A, the direction of a resistive force, which is in a direction normal to the first slanting contact surface 26c in this case, becomes closer to the main axis of the end effector 2, which results in a reduction in resistance. When the end effector 2A is in a pivoted position and the first jaw 21 and the second jaw 22 are in an open state, if the first jaw 21 and the second jaw 22 are closed by an external force and thus the second connection member 26A is pushed down by the first connection member 25 and the end effector manipulation rod 51 is moved backwardly toward the proximal end, the direction of a resistive force, which is in a direction normal to the first slanting contact surface 26c in this case, becomes closer to the main axis of the end effector manipulation rod 51, which results in a reduction in resistance.

Thus in this structure, when the first connection member 25 is pushed up or down by the second connection member 26A, a resistive force is reduced, which allows the first jaw 21 and the second jaw 22 forming the end effector 2A to be opened and closed more smoothly.

The diameter of a hole for receiving the second connection pin 10b of the first connection member 25 may be set to be greater than the diameter of the external diameter of the second connection pin 10b so as to provide a greater clearance. The diameter of a hole for receiving the third connection pin 10c of the end effector manipulation rod 51 may be set to be greater than the diameter of the external diameter of the third connection pin 10c so as to provide a greater clearance. The structures and the operations of the other portions are similar to those according to the first embodiment, and those similar members, denoted by similar reference numerals to those in the first embodiment, are not described in further detail herein.

In the present embodiment, as described above, the first slanting contact surface with which the end face of the flat plate-shaped distal end part of the end effector manipulation rod is in contact and the second slanting contact surface with which the end face of the proximal end part of the first connection member is in contact are provided on the second connection member whereby the direction of the perpendicular resistive force imposed by the first connection member on the second connection member or imposed by the second connection member on the first connection member is made closer to the axis of the end effector manipulation rod, thereby achieving an improvement in operability.

Now, referring to FIGS. 28 to 31, a fourth embodiment of the present invention is described below.

In the end effector 2B according to the present embodiment, the end effector 2B is pivoted in a direction perpendicular to a direction in which the first jaw 21 and the second jaw 22 of the end effector 2B are opened and closed.

To this end, the end effector 2B according to the present embodiment is different from the end effector 2 or 2A according to the previous embodiments. More specifically, as shown in FIGS. 28 and 29, the structure of the end effector base 23A according to the present embodiment is different in structure from the end effector base 23 according to the previous embodiments.

That is, the distal-end projections 23e of the end effector base 23A project in planes perpendicular to the planes in which the distal-end projection 23b of the end effector base 23 project. To adapt to the above modification of the distal-end projections 23e, the first connection member 25A for connecting the proximal end of the second jaw 22 into the recess formed in the distal end part of the second connection member 26 is formed such that the first connection pin 10a and the second connection pin 10b extend in directions perpendicular to each other. The structures and the operations of the other portions are similar to those according to the first embodiment, and those similar members, denoted by similar reference numerals to those in the first embodiment, are not described in further detail herein.

Figure 28:
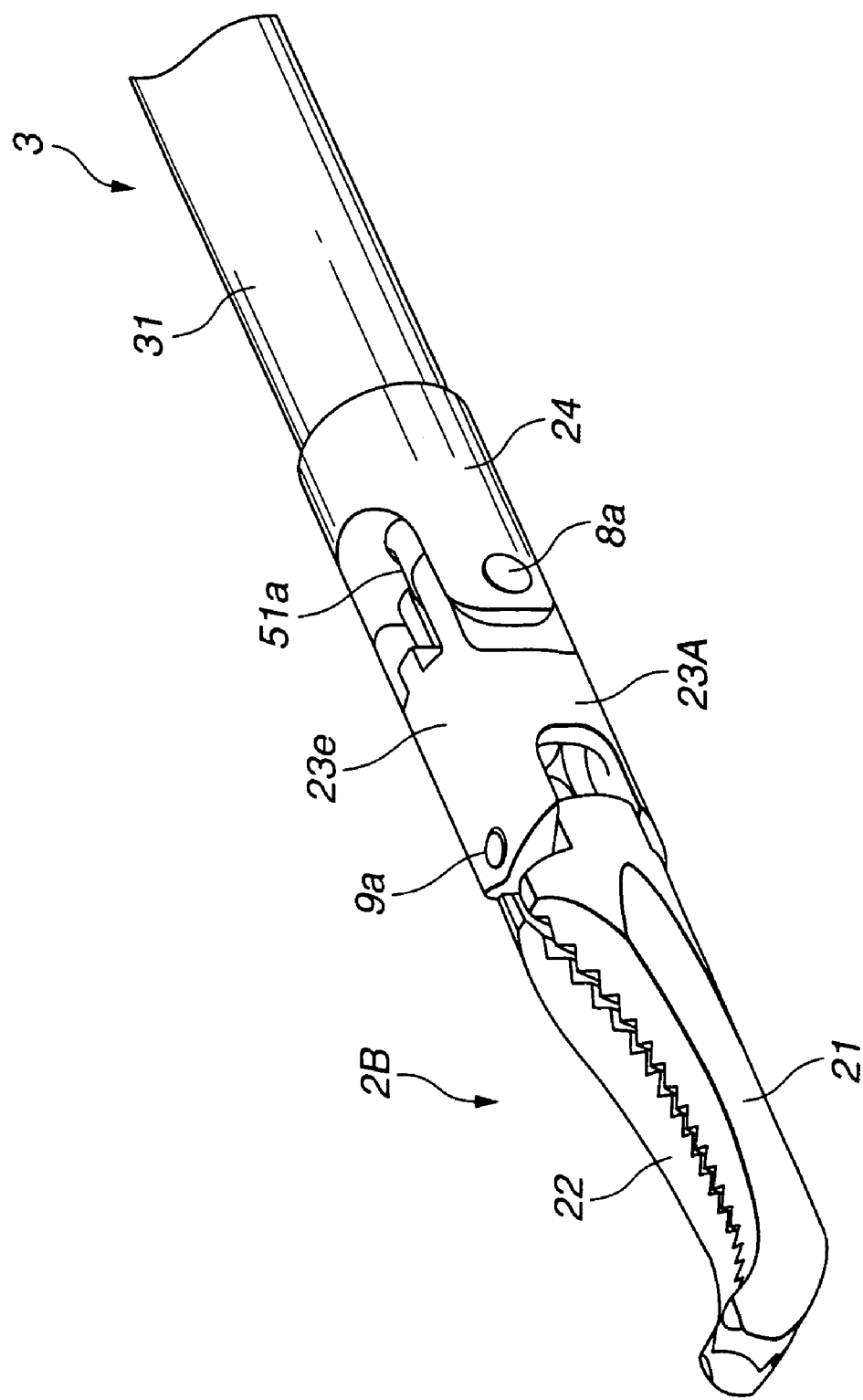
FIG. 28 is a diagram illustrating an end effector including an end effector base having a characteristic structure, in a state in which the end effector is in a position in which the end effector and an insertion portion lie in a straight line.
Figure 29:
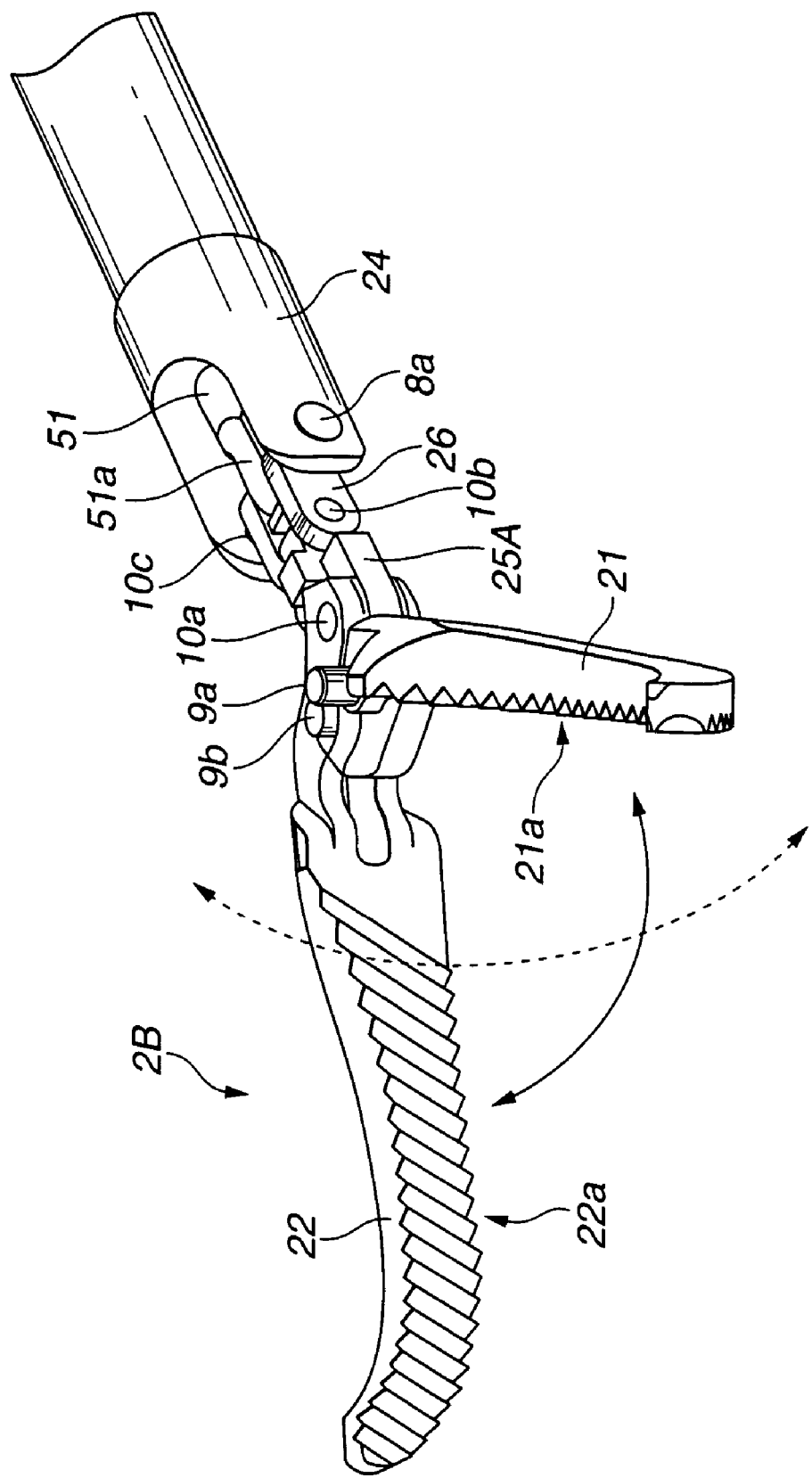
FIG. 29 is a diagram illustrating the end effector in an open state.

In this structure, when the end effector 2B is in a state shown in FIG. 28, if the flat plate-shaped distal end part 51a of the end effector manipulation rod 51 is moved, then the first jaw 21 and the second jaw 22 of the end effector 2B are opened or closed, as indicated by a solid arrow in FIG. 29, in a plane perpendicular to a plane in which the jaws shown in FIG. 13 are opened or closed as indicated by a broken arrow in FIG. 29.

Figure 30:
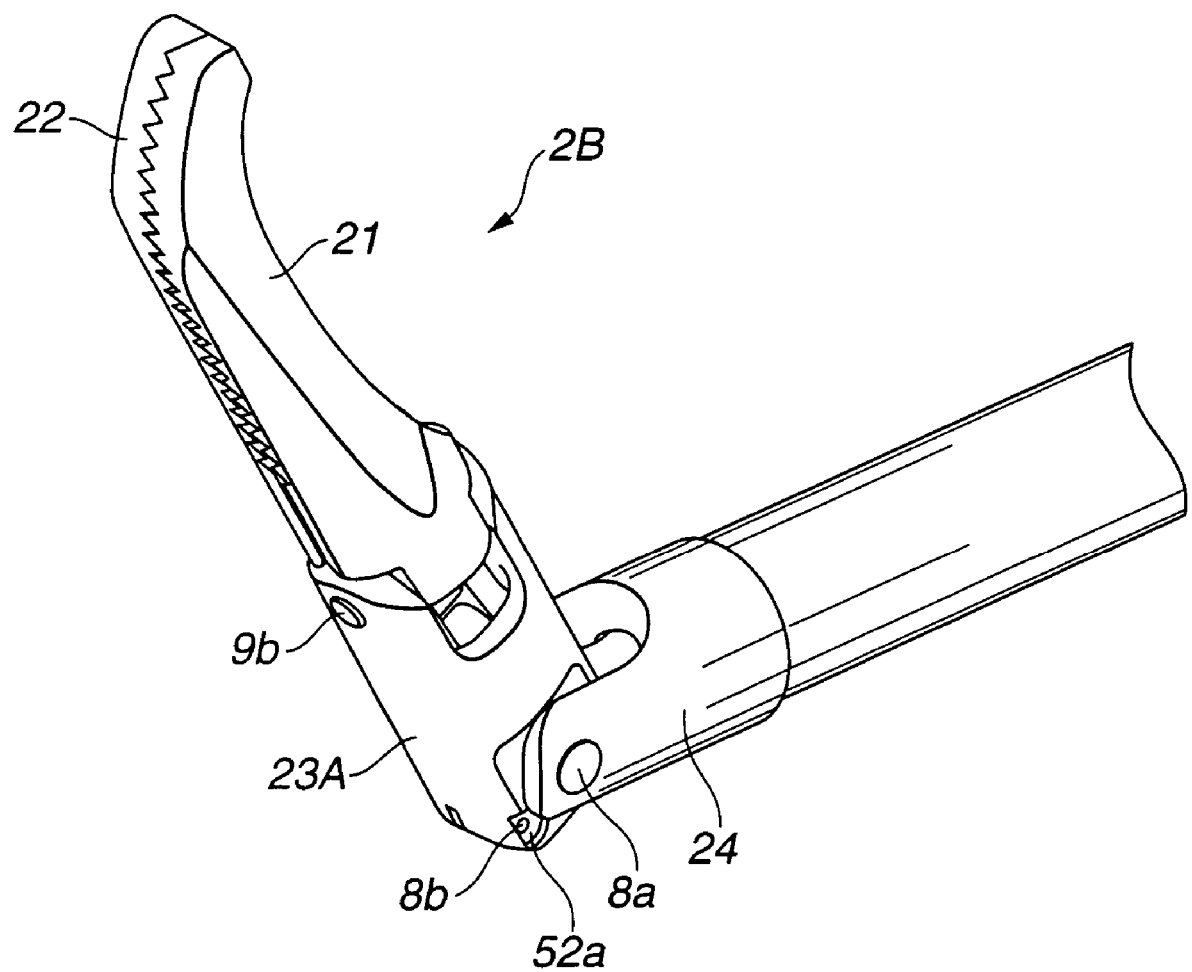
FIG. 30 is a diagram illustrating an end effector in a pivoted position into which the end effector has been moved from a straight position.
Figure 31:
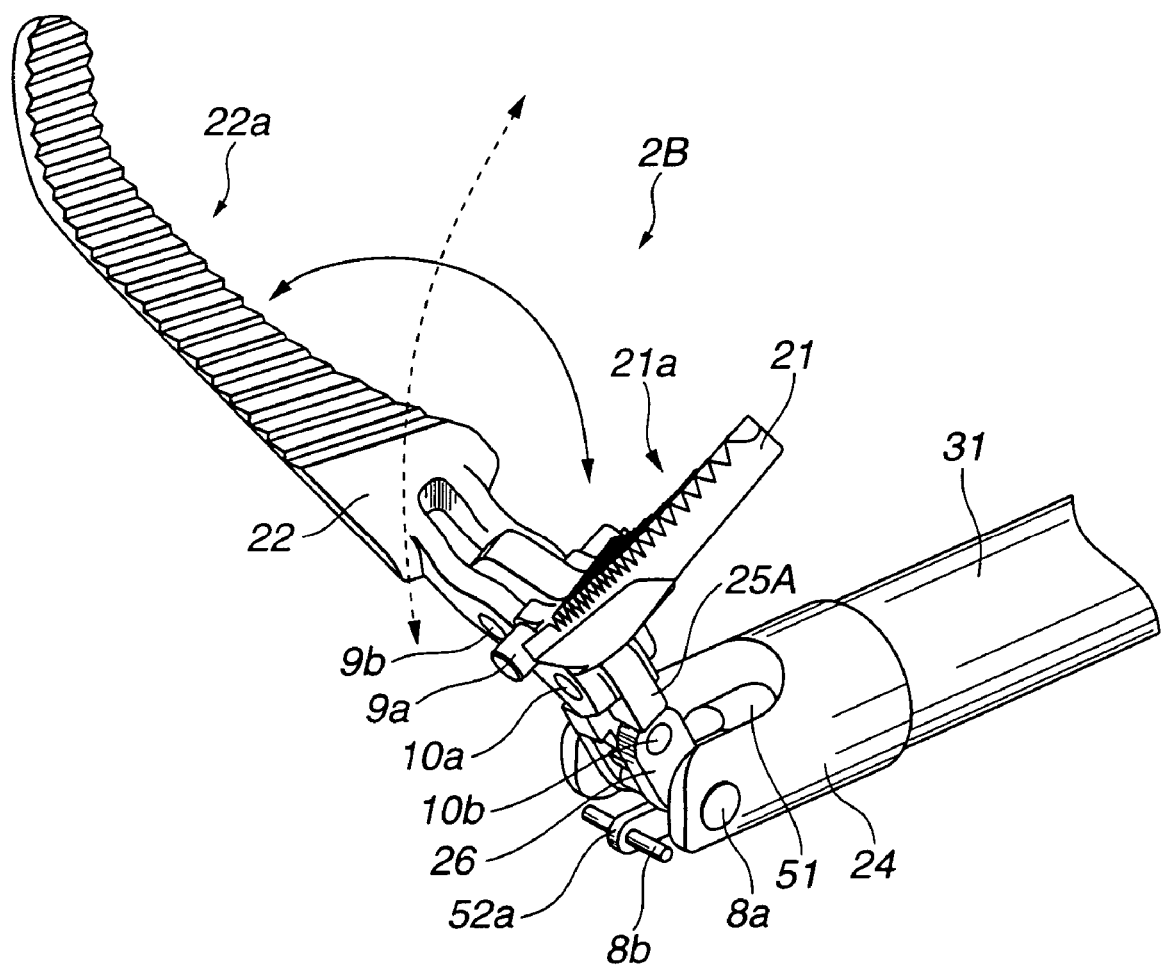
FIG. 31 is a diagram illustrating the end effector in an open state in a pivoted position, wherein an end effector base is removed to provide an easier understanding.

On the other hand, when the end effector 2B is in the state shown in FIG. 28, if the distal end unit 52a of the end effector base manipulation rod 52 is moved, the end effector 2B is moved from the straight position to a pivoted position as shown in FIG. 30. In this pivoted position, if the flat plate-shaped distal end part 51a of the end effector manipulation rod 51 is further moved, then the first jaw 21 and the second jaw 22 of the end effector 2B are opened or closed, as indicated by a solid arrow in FIG. 31, in a plane perpendicular to a plane in which the jaws shown in FIG. 19 are opened or closed as indicated by a broken arrow in FIG. 31.

In the present embodiment, as described above, the pair of jaws of the end effector is opened and closed in a plane perpendicular to a plane in which the end effector pivots. This allows an expansion in a range within which the distal end tool can move, which results in further improvements in operability and utility.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A surgical instrument comprising:
 a tubular member having a distal end and a proximal end, for forming an axis;

a partition member disposed in the tubular member in a direction along the axis of the tubular member, for partitioning the inside of the tubular member;

a first shaft disposed in a first channel formed by the partition member such that the first shaft can move in both forward and backward directions;

a second shaft disposed in a second channel formed by the partition member such that the second shaft can move in both forward and backward directions;

an end effector including a pair of jaws;

a base member connected to the second shaft, for supporting the end effector;

a supporting pin for pivotably supporting the base member to mount the end effector on the distal end of the tubular member;

a first connection member connected to the jaws, the first connection member being movable in both forward and backward directions in the base member to open and close the jaws;

a second connection member for connecting the first connection member with the first shaft, the second connection member being movable through a joint formed by the supporting pin, and including a first insertion hole for receiving a first connection pin for connection with the first connection member and a second insertion hole for receiving a second connection pin for connection with the first shaft; and the second connection member being movable between a location at which the supporting pin and the first insertion hole are coincident with each other and a location at which the supporting pin and the second insertion hole are coincident with each other;

a first operation control portion connected to the first shaft, for manipulating the end effector via the first shaft; and a second operation control portion connected with a proximal end of the second shaft, the second operation control portion moving the second shaft in both forward and backward directions to control the angle of the joint.

2. A surgical instrument according to claim 1, wherein the first operation control portion includes a fixed handle and a movable handle, and wherein a proximal end of the first shaft is detachably connected to the movable handle.

3. A surgical instrument according to claim 1, wherein the second operation control portion is a pivot control knob capable of rotating around the tubular member connected, by means of screwing, with a pivot base integrally fixed to a proximal end part of second shaft, for moving the second shaft in a forward or backward direction in response to the rotation of the pivot control knob.

4. A surgical instrument according to claim 1, wherein the second operation control portion is a backward/forward-moving knob capable of moving in both forward and backward directions relative to the tubular member connected, with a pivot base integrally fixed to a proximal end part of second shaft, for moving the second shaft in a forward or backward direction in response to the motion of the backward/forward-moving knob.

5. A surgical instrument according to claim 1, further comprising a third operation control portion disposed in series to the second operation control portion at a location close to the first operation control portion, the third operation control portion including a rotation control knob for rotating the tubular member as a whole about the axis of the first shaft.

6. A surgical instrument according to claim 5, wherein the two operation control portions disposed in series at the locations close to the first operation control portion are different in external shape such that the external diameter of the knob located farther from the first operation control portion is set to be greater than the external diameter of the knob located closer to the first operation control portion.

7. A surgical instrument according to claim 6, wherein the external diameter, A, of the knob located farther from the first operation control portion and the external diameter, B, of the knob located closer to the first operation control portion are set so as to satisfy the following condition:

$$B < A \leq 2 \times B.$$

8. A surgical instrument according to claim 6, wherein the external diameter, A, of the knob located farther from the first operation control portion and the external diameter, B, of the knob located closer to the first operation control portion are set so as to satisfy the following condition:

$$B < A \leq 1.5 \times B.$$

9. A surgical instrument according to claim 1, wherein the first shaft and the second shaft are formed of a rigid material.

* * * * *